(12) United States Patent
Bunha et al.

(10) Patent No.: US 10,340,091 B2
(45) Date of Patent: Jul. 2, 2019

(54) POLYANION COPOLYMERS FOR USE WITH CONDUCTING POLYMERS IN SOLID ELECTROLYTIC CAPACITORS

(71) Applicant: KEMET Electronics Corporation, Simpsonville, SC (US)

(72) Inventors: Ajaykumar Bunha, Simpsonville, SC (US); Antony P. Chacko, Simpsonville, SC (US); Yaru Shi, Simpsonville, SC (US); Qingping Chen, Simpsonville, SC (US); Philip M. Lessner, Simpsonville, SC (US)

(73) Assignee: KEMET Electronics Corporation, Simpsonville, SC (US)

( * ) Notice: Subject to any disclaimer, the term of this patent is extended or adjusted under 35 U.S.C. 154(b) by 0 days.

(21) Appl. No.: 15/595,137

(22) Filed: May 15, 2017

(65) Prior Publication Data
US 2017/0338047 A1    Nov. 23, 2017

Related U.S. Application Data

(60) Provisional application No. 62/338,778, filed on May 19, 2016.

(51) Int. Cl.
*H01G 9/042* (2006.01)
*H01G 9/00* (2006.01)
*H01G 9/04* (2006.01)
*H01G 9/15* (2006.01)
(Continued)

(52) U.S. Cl.
CPC ........... *H01G 9/042* (2013.01); *H01G 9/0036* (2013.01); *H01G 9/04* (2013.01); *H01G 9/15* (2013.01); *H01M 4/136* (2013.01); *H01M 4/137* (2013.01); *H01G 2009/0014* (2013.01); *H01G 2009/0404* (2013.01)

(58) Field of Classification Search
None
See application file for complete search history.

(56) References Cited

U.S. PATENT DOCUMENTS

| | | | |
|---|---|---|---|
| 5,280,078 A | 1/1994 | Gregor et al. |
| 5,300,575 A | 4/1994 | Jonas et al. |
| 6,000,840 A | 12/1999 | Paterson |

(Continued)

FOREIGN PATENT DOCUMENTS

WO    WO 2010/089111    8/2010

OTHER PUBLICATIONS

Li et al. Conducting Poiymer Nanomaterials; Electrosynthesis and Applications in Chem. Soc. Rev '09, vol. 38, p. 2307-2409; abst. p. 2401; col. 2; para 4; og 2404; col. 2 par 1.

(Continued)

*Primary Examiner* — Katie L. Hammer
(74) *Attorney, Agent, or Firm* — Joseph T. Guy; Patent Filing Specialist, Inc.

(57) ABSTRACT

A capacitor and a method of making a capacitor, is provided with improved reliability performance. The capacitor comprises an anode; a dielectric on the anode; and a cathode on the dielectric wherein the cathode comprises a conductive polymer and a polyanion wherein the polyanion is a copolymer comprising groups A, B and C represented by Formula $A_xB_yC_z$ as described herein.

120 Claims, 7 Drawing Sheets

(51) Int. Cl.
   *H01M 4/136*       (2010.01)
   *H01M 4/137*       (2010.01)

(56) References Cited

U.S. PATENT DOCUMENTS

| | | |
|---|---|---|
| 7,270,871 B2 | 9/2007 | Jiang et al. |
| 7,563,290 B2 | 7/2009 | Qiu et al. |
| 7,754,276 B2 | 7/2010 | Qiu et al. |
| 7,990,683 B2 | 8/2011 | Qiu et al. |
| 7,990,684 B2 | 8/2011 | Sugihara et al. |
| 9,030,806 B2 | 5/2015 | Chacko et al. |
| 2006/0236531 A1 | 10/2006 | Merker et al. |
| 2011/0049433 A1 | 3/2011 | Jonas et al. |
| 2012/0300370 A1 | 11/2012 | Chacko |
| 2013/0188295 A1* | 7/2013 | Chacko .............. H01G 9/0029 361/525 |
| 2014/0211374 A1* | 7/2014 | Sugihara .............. C08L 65/00 361/527 |
| 2015/0029642 A1 | 1/2015 | Shi et al. |

OTHER PUBLICATIONS

ISA/US; ISR and Written Opinion prepared for PCT/US2017/032704; Applicant: KEMET Electronics Corporation; completed: Jul. 17, 2017; dated Aug. 22, 2017.

* cited by examiner

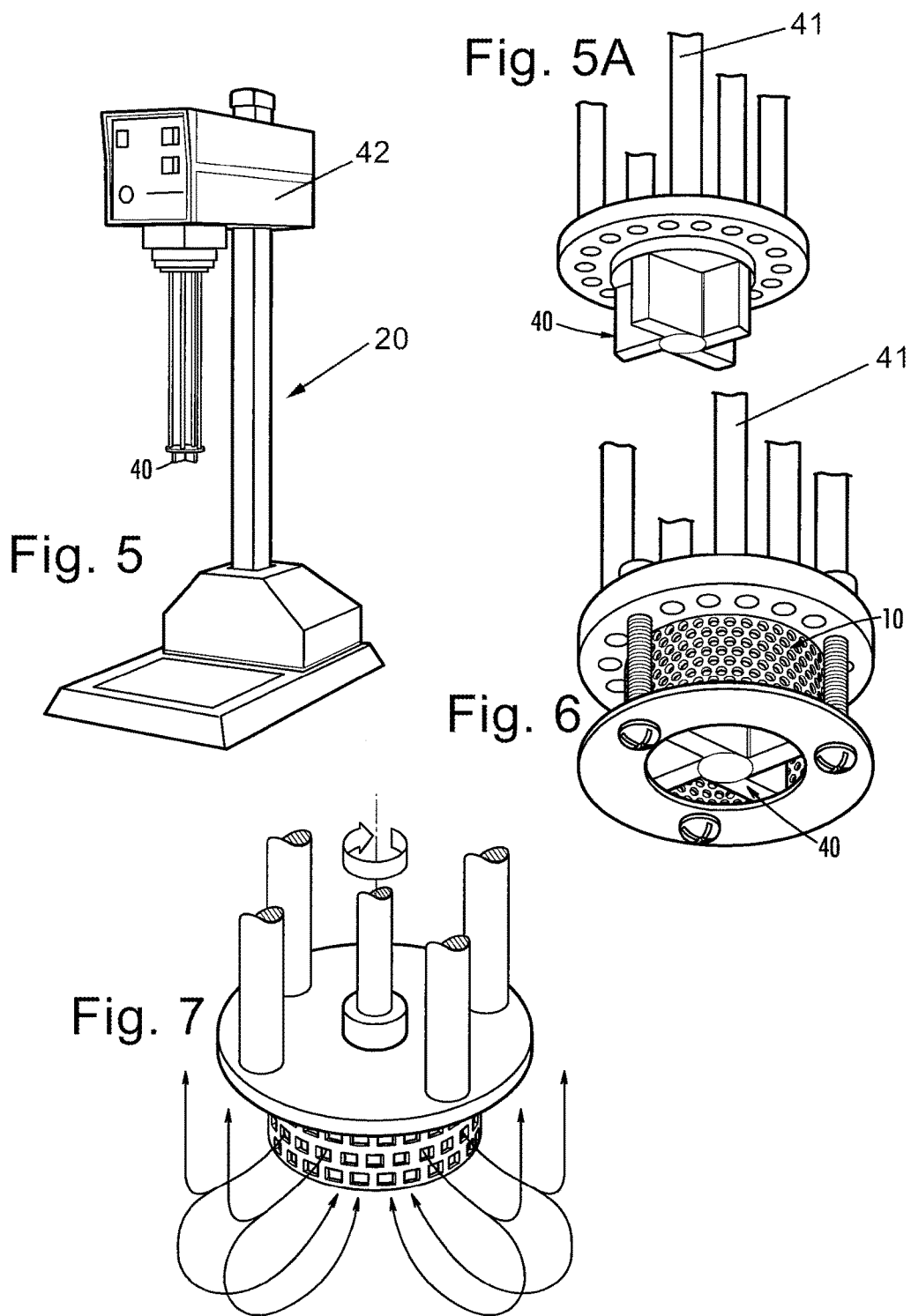

POLYANION COPOLYMERS FOR USE WITH CONDUCTING POLYMERS IN SOLID ELECTROLYTIC CAPACITORS

CROSS-REFERENCE TO RELATED APPLICATIONS

The present application claims priority to U.S. Provisional Patent Application No. 62/338,778 filed May 19, 2016 which is incorporated herein by reference.

BACKGROUND

The present invention is related to improved polyanions which are particularly suitable for use with conducting polymers and especially as part of a cathode of a solid electrolytic capacitor.

Solid electrolytic capacitors are widely used throughout the electronics industry. In high voltage applications solid electrolytic capacitors with a solid electrolyte, formed by conductive polymer dispersions, give excellent high voltage performance compared to conductive polymer cathodes formed in-situ. These conductive polymer dispersions are prepared by a number of process steps including polymerization, purification, filtration, homogenization, evaporation, etc. Descriptions of these processes are provided in U.S. Pat. Nos. 5,300,575; 7,990,684; 7,270,871; 6,000,840 and 9,030,806; U.S. Patent Publication No. 2011/0049433 and PCT Publication WO 2010/089111 each of which is incorporated herein by reference.

Capacitors and methods of making capacitors are provided in U.S. Pat. Nos. 7,990,683; 7,754,276 and 7,563,290 each of which is incorporated herein by reference.

Solid electrolytic capacitors comprising conducting polymer, as the cathode, have several disadvantages. For example, solid electrolytic capacitors suffer from poor equivalent series resistance (ESR) particularly under high humidity and high temperature conditions. In addition, poor coverage of conducting polymers on corners and edges of anodized anode results in high DC leakage current. One approach for improving coverage of the corners and edges is provided in International Application WO2010089111A1, which is incorporated herein by reference, which describes a group of chemical compounds called crosslinkers or primer, which are mostly multi-cationic salts or amines. International Application WO2010089111A1 teaches the application of a solution of the crosslinker on the anodized anode prior to the application of polymer slurry to achieve good polymer coverage on corners and edges of the anodized anode. The effectiveness of the crosslinker is attributed to the cross-linking ability of multi-cationic salts or amines to the slurry/dispersion particles. While crosslinkers are advantageous for improving the coating coverage on corners and edges of the anodized anode, the addition of these crosslinkers, which are mostly ionic in nature, has the unintended consequences of degrading the humidity performance of a finished product.

Many of the problems associated with solid electrolytic capacitors have now been found to be the result of the nature of the conductive polymeric layer and particularly the polyanion counterion of the conductive polymer. The strongly acidic nature of polyanions also contributes to increased moisture absorption leading to additional problems such as increased corrosion of metals in a capacitive device. The dispersions of conductive polymer and polyanion are also typically not effective at forming an adequate coating on the dielectric which often leads to thin, or vacant, coatings thereby leading to poor leakage current. Thus, additional binders/additives in conducting polymer dispersions are required to maintain film strength during fabrication and device operation. Moreover, higher the percent solids in conductive polymer dispersion are desired to improve corner/edge coating coverage of anodized anode and possibly minimize/eliminate use of ionic cross-linker/primer.

It has been found that the use of polyanion copolymer with lower concentration of sulfonic acid groups and containing performance enhancement functional groups such as adhesion promoter/moisture retention/hydrophobic/cross-linkable groups can mitigates the above problems.

The present invention sets forth improvements in the polyanion, method of making the polyanion and conductive polymer dispersions comprising the polyanion.

SUMMARY OF THE INVENTION

It is an object of the invention to provide an improved polyanion which is particularly suitable for use as a counterion for a conductive polymer and particularly as a component of a conductive cathode layer in a solid electrolytic capacitor.

It is another object of the invention to reduce sulfonic acid concentration in a polyanion through the use of copolymer composition containing performance enhancement functional groups.

It is further an object of invention to reduce moisture absorption of conducting polymer layers.

It is also an object of invention to improve corners/edges coverage of the anodized anodes, when forming solid electrolytic capacitors, through improved polyanion compositions.

It is also an object of invention to increase the percent solids in a conducting polymer dispersion while retaining viscosity below the processable limit.

It is also an object of the invention to provide an improved polyanion which is particularly suitable for improving film forming properties of the conducting polymer dispersion comprising intrinsically conducting polymer and polyanion counterion.

These and other advantages, as will be realized, are provided in a capacitor comprising: an anode; a dielectric on the anode; and a cathode on the dielectric wherein the cathode comprises a conductive polymer and a polyanion wherein the polyanion is a copolymer comprising groups A, B and C represented by Formula $A_xB_yC_z$ as described herein.

Yet another embodiment is provided in a method for forming a capacitor comprising: forming an anode; forming a dielectric on said anode; forming a cathode on said dielectric wherein said cathode comprises: a conductive polymer; and a polyanion wherein said polyanion is a copolymer comprising groups A, B and C represented by the $A_xB_yC_z$ as described herein.

Yet another embodiment is provided in a slurry comprising a conductive polymer; and a polyanion wherein said polyanion is a copolymer comprising groups A, B and C represented by the $A_xB_yC_z$ as described herein.

BRIEF DESCRIPTION OF FIGURES

FIG. 5 is a schematic perspective view of a mixer.

FIG. 5A is a schematic perspective bottom view of a portion of FIG. 5.

FIG. 6 is a schematic perspective bottom view of a portion of a mixer.

FIG. 7 is a schematic flow diagram of material in a mixer.

DESCRIPTION

Figure 1:
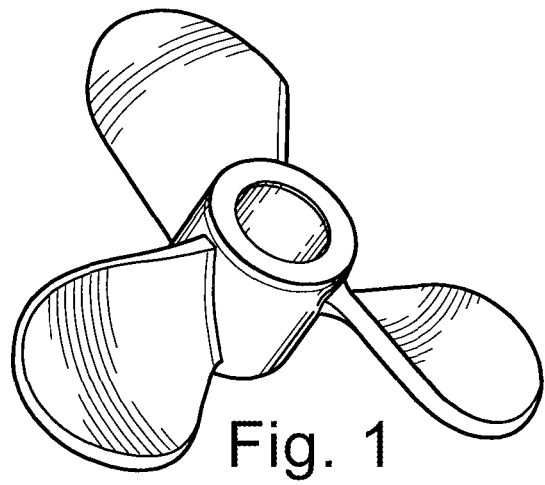
FIG. 1 is a schematic perspective view of a mixing impeller.

The present invention is related to improved conductive polymer dispersions and particularly improved polyanions as the counterion of the intrinsically conducting polymers and polymer dispersions formed with the polyanions. More particularly, the present invention is related to improved polyanions comprising a copolymer comprising polystyrene sulfonic acid groups, and other functional groups which provide adhesion promotion, humidity resistance, robust film formation through inter/intra molecular cross-linking, controlled moisture absorption and other performance improvements. The dispersions comprising improved polyanions are particularly suitable for use in the formation of a cathode in a solid electrolytic capacitor.

The invention will be described with reference to the various figures which are an integral, non-limiting, component of the disclosure.

The inventive polyanion is a, preferably, random copolymer comprising groups A, B and C represented by the ratio of Formula A:

$$A_x B_y C_z \qquad \text{Formula A}$$

wherein:

A is polystyrenesulfonic acid or salt of polystyrenesulfonate;

B and C separately represent polymerized units substituted with a group selected from:

-Carboxyl groups;

—C(O)OR$^6$ wherein R$^6$ is selected from the group consisting of:
  an alkyl of 1 to 20 carbons optionally substituted with a functional group selected from the group consisting of hydroxyl, carboxyl, amine, epoxy, silane, amide, imide, thiol, alkene, alkyne, azide, phosphate, acrylate, anhydride and
  —(CHR$^7$CH$_2$O)$_b$—R$^8$ wherein:
    R$^7$ is selected from a hydrogen or an alkyl of 1 to 7 carbons and preferably hydrogen or methyl;
    b is an integer from 1 to the number sufficient to provide a molecular weight of up to 200,000 for the —CHR$^7$CH$_2$O— group; and
    R$^8$ is selected from the group consisting of hydrogen, silane, phosphate, acrylate, an alkyl of 1 to 9 carbons optionally substituted with a functional group selected from the group consisting of hydroxyl, carboxyl, amine, epoxy, silane, amide, imide, thiol, alkene, alkyne, phosphate, azide, acrylate, and anhydride;

—C(O)—NHR$^9$ wherein:
  R$^9$ is hydrogen or an alkyl of 1 to 20 carbons optionally substituted with a functional group selected from the group consisting of hydroxyl, carboxyl, amine, epoxy, silane, amide, imide, thiol, alkene, alkyne, phosphate, azide, acrylate and anhydride;

—C$_6$H$_4$—R$^{10}$ wherein:
  R$^{10}$ is selected from:
    a hydrogen or alkyl optionally substituted with a functional group selected from the group consisting of hydroxyl, carboxyl, amine, epoxy, silane, amide, imide, thiol, alkene, alkyne, phosphate, azide, acrylate and anhydride;
    a reactive group selected from the group consisting of hydroxyl, carboxyl, amine, epoxy, silane, imide, amide, thiol, alkene, alkyne, phosphate, azide, acrylate, anhydride and
    —(O(CHR$^{11}$CH$_2$O)$_d$—R$^{12}$ wherein:
      R$^{11}$ is a hydrogen or an alkyl of 1 to 7 carbons and preferably hydrogen or methyl;
      d is an integer from 1 to the number sufficient to provide a molecular weight of up to 200,000 for the —CHR$^{11}$CH$_2$O— group;
      R$^{12}$ is selected from the group consisting of hydrogen, an alkyl of 1 to 9 carbons optionally substituted with a functional group selected from the group consisting of hydroxyl, carboxyl, amine, epoxy, silane, amide, imide, thiol, alkene, alkyne, phosphate, azide, acrylate and anhydride;

—C$_6$H$_4$—O—R$^{13}$ wherein:
  R$^{13}$ is selected from:
    a hydrogen or an alkyl optionally substituted with a reactive group selected from the group consisting of hydroxyl, carboxyl, amine, epoxy, silane, amide, imide, thiol, alkene, alkyne, azide, acrylate, phosphate and anhydride;
    a reactive group selected from the group consisting of epoxy, silane, alkene, alkyne, acrylate, phosphate and
    —(CHR$^{14}$CH$_2$O)$_e$—R$^{15}$ wherein:
      R$^{14}$ is a hydrogen or an alkyl of 1 to 7 carbons and preferably hydrogen or methyl;
      e is an integer from 1 to the number sufficient to provide a molecular weight of up to 200,000 for the —CHR$^{14}$CH$_2$O— group; and
      R$^{15}$ is selected from the group consisting of hydrogen and an alkyl of 1 to 9 carbons optionally substituted with a functional group selected from the group consisting of hydroxyl, carboxyl, amine, epoxy, silane, amide, imide, thiol, alkene, alkyne, azide, acrylate, phosphate and anhydride;

x, y and z, taken together are sufficient to form a polyanion with a molecular weight of at least 100 to no more than 500,000 and y/x is 0.01 to 100; z is 0 to a ratio z/x of no more than 100; more preferably x represents 50-99%, y represents 1 to 50% and z represents 0 to 49% of the sum total of x+y+z; even more preferably x represents 70-90%; y represents 10 to 30% and z represents 0 to 20% of the sum total of x+y+z; and with the proviso that C is not same as B and z is not zero when B is substituted with a group selected from:

—C(O)OR$^6$ wherein:
  R$^6$ is H or an alkyl substituted with hydroxyl, epoxy or silane group, $(CHR^7CH_2O)_b$—$R^8$ wherein:

$R^7$ is H and $R^8$ is phosphate group;

—$C_6H_4$—$R^{10}$ wherein:

$R^{10}$ is hydrogen or an alkyl of 1-30 carbon.

In one embodiment the inventive polyanion functions as a coating aid with insufficient polystyrene sulfonic acid groups to function as an efficient counterion to the conductive polymer. In this instance it is preferable that in the inventive polyanion represented by Formula A wherein x represents 1-40%, y represents 60 to 99% and z represents 0 to 39% of the sum total of x+y+z; even more preferably x represents 5 to 40%; y represents 60 to 95% and z represents 0 to 35% of the sum total of x+y+z.

Particularly preferred polyanions include:

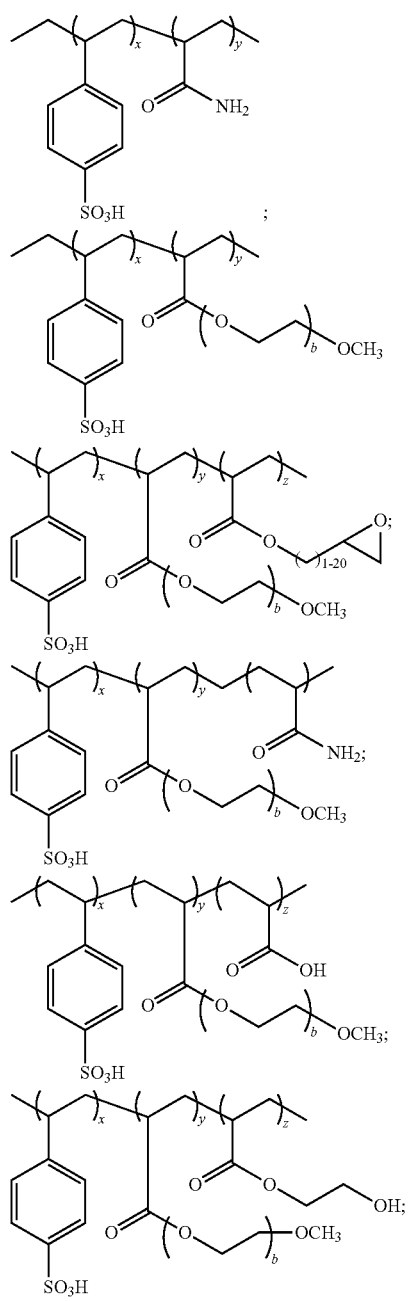

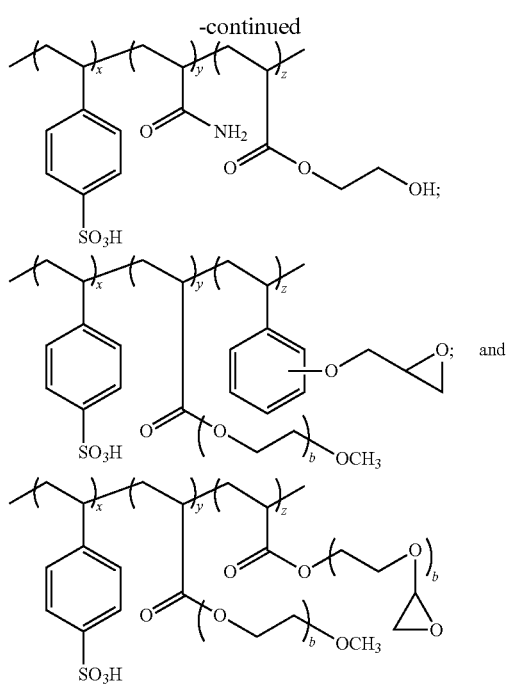

wherein b, x, y and z are as defined above.

The polyanion copolymers are preferably synthesized by a free radical polymerization method. By way of non-limiting example, different ratios of salt of styrene sulfonic acid, to form component A of Formula A, and the appropriate monomers for formation of components B and C of Formula A, are polymerized in the presence of free radical initiator at high temp (ranges from 25° C. to 150° C.) and under inert atmospheric condition.

The solvent in which the monomer(s) are to be dissolved is preferably water. A water-soluble solvent may be used, or a mixture of water and a water-soluble solvent may be used. The water-soluble solvent is not particularly limited. Examples of the solvent include acetone, tetrahydrofuran, methanol, ethanol, isopropanol, and N-methyl-2-pyrrolidone.

Figure 10:
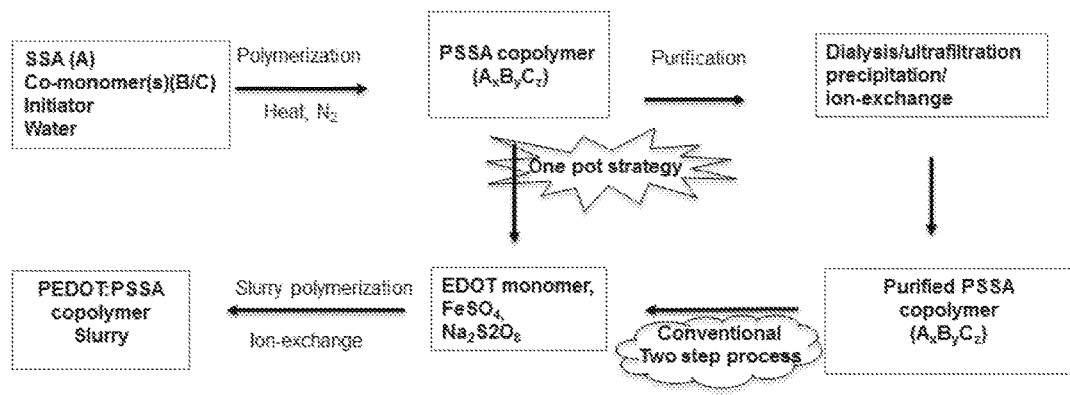
FIG. 10 is a schematic representation of conductive polymer dispersion preparation through inventive "one pot" versus conventional (two step) process.

The polymerization initiator is not particularly limited, and may be, for example, a peroxide, or an azo compound. Examples of the peroxide include ammonium persulfate, potassium persulfate, hydrogen peroxide, cumene hydroperoxide, and di-t-butylperoxide. Examples of the azo compound include 2,2-azobis(4-methoxy-2,4-dimethylvaleronitrile), 2,2'-azobis(2,4-dimethylvaleronitrile), and 2,2'-azobisisobutyronitrile. The polyanion copolymer can be used directly without further purification in the preparation of conductive polymer dispersion as referred here "one pot synthesis strategy" as described in FIG. 10. Moreover, the polyanion copolymer can be purified, preferably by dialysis, precipitation, ultrafiltration or ion exchange method prior to the preparation of conductive polymer dispersion through a conventional "two step synthesis techniques".

The conductive polymer dispersion can be prepared in accordance with U.S. Pat. No. 9,030,806 which is incorporated herein by reference. The preferred polymerization method uses a stator screen which provides a uniform droplet size resulting in average polymer particle sizes below about 200 nm, more preferably 150 nm and even more preferably below about 100 nm.

Conductive polymer dispersions having a lower, and controllable, average particle size can be prepared during polymerization, without additional process steps, when the polymerization is carried out using a rotor stator mixing system with perforated screen stators preferably with hole diameters below about 6 mm. The dispersion may further comprise at least one polyanion copolymer.

Figure 2:
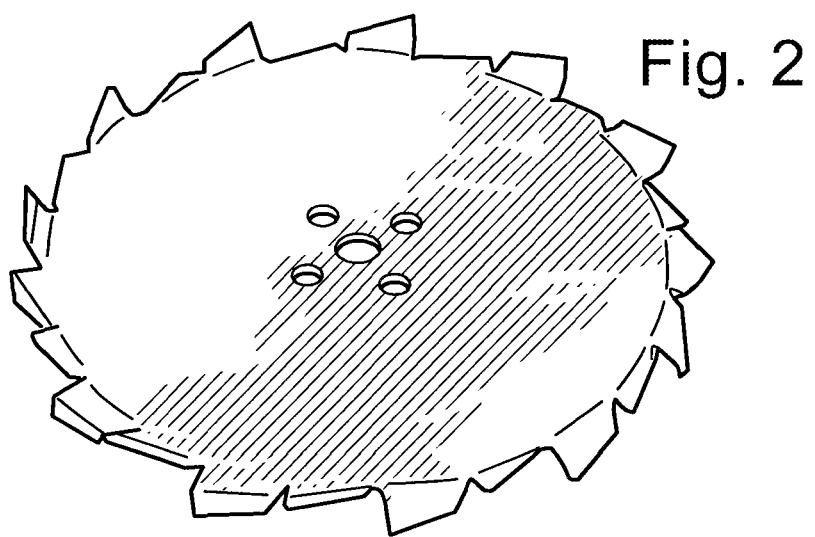
FIG. 2 is a schematic perspective view of a high shear impeller.
Figure 3:
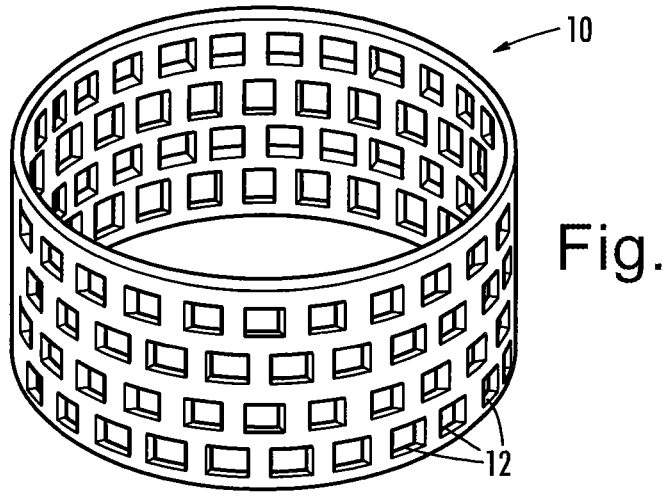
FIG. 3 is a schematic perspective view of square hole perforated stator screen.
Figure 4:
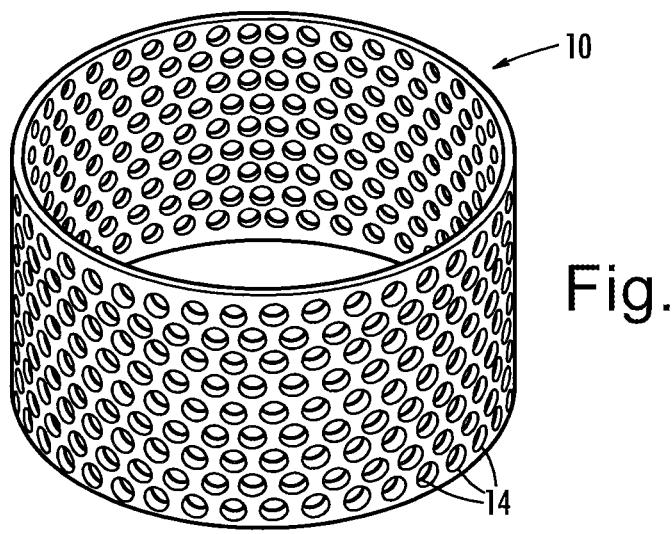
FIG. 4 is a schematic perspective view of a circular hole perforated stator screen.

FIGS. 1 and 2 illustrate mixing impellers which can be used but typically offer poor control over average particle size of the polymer. FIGS. 3 and 4 illustrate preferred stator screens, 10, with square holes, 12, and circular holes, 14. The stator screens, 10, are preferably cylindrical and arranged relative to a paddle impeller in an orientation such that material will be forced through the stator screen thereby imparting shear on the material. The stator screens diameter is selected to provide sufficient tip speed to achieve sufficient shear. Tip Speed is defined as:

$$\text{Tip speed} = \pi \times D \times N$$

wherein:
π is a known constant which is the ratio of a circle's circumference to its diameter;
D is the equivalent diameter of the rotor; and
N is the rotation rate of the mixer.

Figure 8:
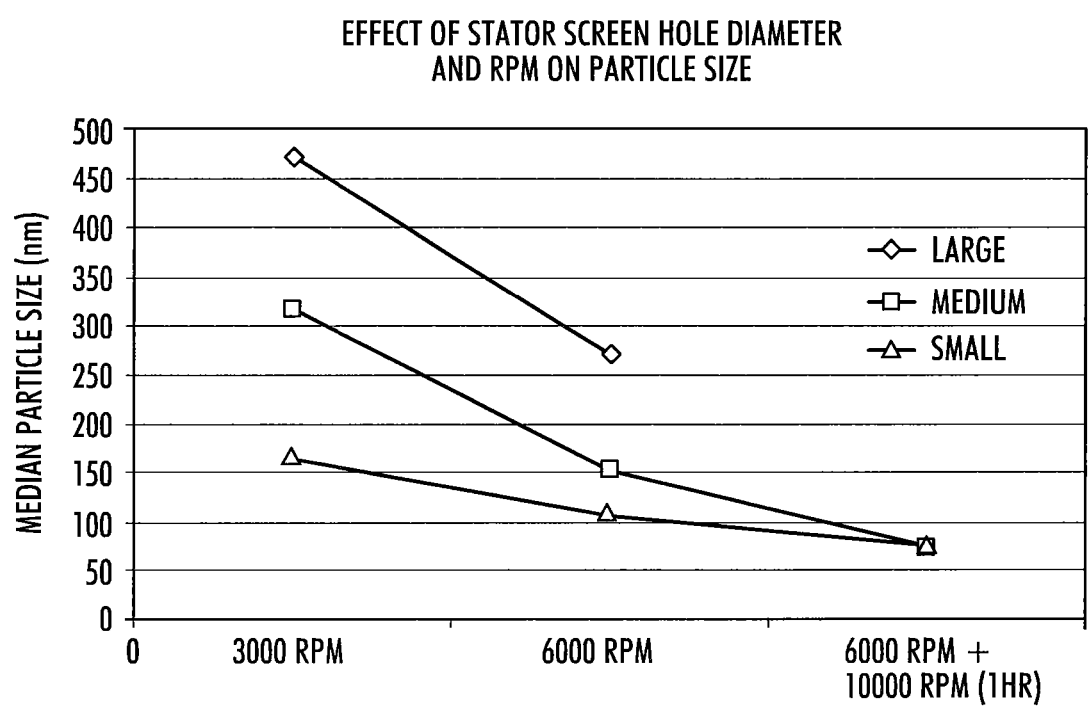
FIG. 8 is a graphical illustrations of advantages of particle size as a function of RPM.

As illustrated in FIG. 8, the larger the hole size the higher the rotation rate necessary to achieve adequate shear and average particle size wherein 3000 rpm represents a shear rate of about 21,800 sec$^{-1}$; 6,000 rpm represents a shear rate of about 43,600 sec$^{-1}$ and 10,000 rpm represents a shear rate of about 72,600 sec$^{-1}$. FIG. 8 illustrates the relation between average particle size and rotational speed using a Silverson lab mixer L5MA with a rotor diameter of 1.2 inches, stator screen with large (6 mm), medium (2.4 mm), and small (1.6 mm) holes.

Shear rate is defined herein as the tip speed/rotor stator gap. By way of example, for a rotor diameter of 3.175 cm (1.25 inches) and rotational speed of 6,000 RPM the tip speed is 12.8 m/min (42 ft/minute). With a rotor gap of 0.228 mm (0.009 inches) the shear rate is calculated as 51000 sec$^{-1}$. The shear rate is preferably at least about 10,000 to 800,000 sec$^{-1}$ and more preferably at least 40,000 to 75,000 sec$^{-1}$.

Rotor/stator mixers comprise a rotor turning at high speeds within a stationary stator. As the blades rotate, materials are continuously drawn into one end of the mixing head and expelled at high velocity through the openings of the stator. The resulting hydraulic shear reduces the size of suspended droplets. Inline high shear mixers are used in an inline configuration wherein they behave like a centrifugal pump. The basic single-stage inline high shear mixer consists of a four-blade rotor that turns at high speeds within a stationary stator. Rotor tip speeds between 914 to 1,219 m/min (3,000 to 4,000 ft/min.) are typical. Rotor/stator mixers are offered with a variety of interchangeable stator designs.

The "multi-stage" rotor/stator consists of 2-4 rotor/stator pairs nested concentrically, mix material moves outward from the center of the multi-stage unit, and it is subjected to a quick succession of shearing events. Examples of the multistage rotor/stator mixer are the ultrahigh shear rate mixers. The X-Series head from Charles Ross and Sons and exemplified in U.S. Pat. No. 5,632,596, consists of concentric rows of intermeshing teeth. The droplets enter at the center of the stator and move outward through radial channels in the rotor/stator teeth. The combination of extremely close tolerances and very high tip speeds, 3,444 m/min (11,300 fpm) or higher, subjects the droplets to intense shear in every pass through the rotor/stator. The gap between adjacent surfaces of the rotor and stator are adjustable from 0.254 to 4.57 mm (0.010" to 0.180") for very high shear rates such as 750,000 sec$^{-1}$.

The MegaShear head, exemplified in U.S. Pat. No. 6,241,472, is capable of the highest peak shear and throughput levels. It consists of parallel semi-cylindrical grooves in the rotor and stator towards which product is forced by high velocity pumping vanes. Different streams are induced within the grooves which collide at high frequency before exiting the mix chamber.

Such high shear batch, inline, single stage, and multistage rotor-stator mixers are available from various vendors including Charles Ross & sons, Silverson, etc.

The creation of small particle sizes during polymerization is believed to involve the generation of small droplets of monomer through a combination of mechanical energy using a rotor-stator mixing system to manipulate the droplet size with an appropriate choice of perforated stator screens, with specific holes having specific equivalent diameters. It is preferable to stabilize the resulting droplets with surfactant. In conventional polymerization the monomer droplets are large which limits the particle size of the polymer. A mixing system in which the mixer produces intense hydraulic shear wherein the monomer droplets are forced through perforations in the stator screen reduces the monomer droplets into very small droplet sizes. The very small monomer droplets are stabilized by polyanions and the polymerization is believed to be initiated around the monomer droplet wherein the droplet size during polymerization is correlated to the polymer particle size.

Though not limited thereto, the present invention is particularly suitable for use in forming conductive polymers of polyanilines, polypyrroles and polythiophenes each of which may be substituted. The preferred monomer for polymerization is described in Formula 1:

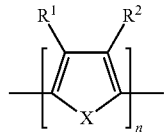

Formula 1 wherein:
$R^1$ and $R^2$ independently represent linear or branched $C_1$-$C_{16}$ alkyl or $C_2$-$C_{18}$ alkoxyalkyl; or are $C_3$-$C_8$ cycloalkyl, phenyl or benzyl which are unsubstituted or substituted by $C_1$-$C_6$ alkyl, $C_1$-$C_6$ alkoxy, halogen or $OR^3$; or $R^1$ and $R^2$, taken together, are linear $C_1$-$C_6$ alkylene which is unsubstituted or substituted by $C_1$-$C_6$ alkyl, $C_1$-$C_6$ alkoxy, halogen, $C_3$-$C_8$ cycloalkyl, phenyl, benzyl, $C_1$-$C_4$ alkylphenyl, $C_1$-$C_4$ alkoxyphenyl, halophenyl, $C_1$-$C_4$ alkylbenzyl, $C_1$-$C_4$ alkoxybenzyl or halobenzyl, 5-, 6-, or 7-membered heterocyclic structure containing two oxygen elements. $R^3$ preferably represents hydrogen, linear or branched $C_1$-$C_{16}$ alkyl or $C_2$-$C_{18}$ alkoxyalkyl; or are $C_3$-$C_8$ cycloalkyl, phenyl or benzyl which are unsubstituted or substituted by $C_1$-$C_6$ alkyl;
X is S, N or O and most preferable X is S;
$R^1$ and $R^2$ of Formula 1 are preferably chosen to prohibit polymerization at the 3-site of the ring as it is most preferred that only α-site polymerization be allowed to proceed; it is more preferred that $R^1$ and $R^2$ are not hydrogen and more preferably, $R^1$ and $R^2$ are α-directors with ether linkages being preferable over alkyl linkages; it is most preferred that the $R^1$ and $R^2$ are small to avoid steric interferences.

In a particularly preferred embodiment the $R^1$ and $R^2$ of Formula I are taken together to represent —O—$(CHR^4)_n$—O— wherein:
n is an integer from 1 to 5 and most preferably 2;
$R^4$ is independently selected from hydrogen; a linear or branched $C_1$ to $C_{18}$ alkyl radical $C_5$ to $C_{12}$ cycloalkyl radical, $C_6$ to $C_{14}$ aryl radical $C_7$ to $C_{18}$ aralkyl radical or $C_1$ to $C_4$ hydroxyalkyl radical, optionally substituted with a functional group selected from carboxylic acid, hydroxyl, amine, substituted amines, alkene, acrylate, thiol, alkyne, azide, sulfate, sulfonate, sulfonic acid, imide, amide, epoxy, anhydride, silane, and phosphate; hydroxyl radical; or $R^4$ is selected from —$(CHR^5)_a$—$R^{16}$; —$O(CHR^5)_a R^{16}$; —$CH_2O(CHR^5)_a R^{16}$; —$CH_2O(CH_2CHR^5O)_a R^{16}$, or
$R^4$ is a functional group selected from the group consisting of hydroxyl, carboxyl, amine, epoxy, amide, imide, anhydride, hydroxymethyl, alkene, thiol, alkyne, azide, sulfonic acid, benzene sulfonic acidsulfate, $SO_3M$, anhydride, silane, acrylate and phosphate;
$R^5$ is H or alkyl chain of 1 to 5 carbons optionally substituted with a functional groups selected from carboxylic acid, hydroxyl, amine, alkene, thiol, alkyne, azide, epoxy, acrylate and anhydride;
$R^{16}$ is H or $SO_3M$ or an alkyl chain of 1 to 5 carbons optionally substituted with a functional groups selected from carboxylic acid, hydroxyl, amine, substituted amines, alkene, thiol, alkyne, azide, amide, imide, sulfate, $SO_3M$, amide, epoxy, anhydride, silane, acrylate and phosphate;
a is integer from 0 to 10; and
M is a H or cation preferably selected from ammonia, sodium or potassium.

The conducting polymer is preferably chosen from polypyrroles, polyanilines, polythiophenes and polymers comprising repeating units of Formula I, particularly in combination with organic sulfonates. A particularly preferred polymer is 3,4-polyethylene dioxythiophene (PEDOT).

The polyanion copolymer of Formula A can be used as counterion to poythiophenen comprising repeating units of Formula I. The ratio of PEDOT to polyanion copolymer in dispersion can be in a range of 1:0.1 to 1:10, more preferably 1:1 to 1:5. The a preferred molecular weight of polyanion at least about 100 to no more than about 500,000. Below a molecular weight of about 100 film integrity can be affected and above a molecular weight of about 500,000 conductivity and viscosity can be adversely affected.

The viscosity of the polymer dispersion is preferably at least 200 cP@20 RPM to no more than 4000 cP@20 RPM at ambient temperature and preferably at least 600 cP@ 20 RPM to no more than 2000 cP@20 RPM at ambient temperature. The dispersion has a preferred percent solids of 1 wt % to no more than 5 wt %. Above about 5 wt % the dispersion does not flow adequately for forming a conductive layer. More preferably, the polymer dispersion has a percent solids of at least 2 wt % to no more than 3.5 wt %.

The dispersion, and polymerization preferably occurs at a temperature of at least about 15° C. to no more than about 35° C. Below a temperature of about 15° C. the polymerization rate is very slow and above about 35° C. conductivity and viscosity can be adversely affected.

The dispersions comprising intrinsically conductive polymer (ICP) and polyanion can be further stabilized by polymeric steric stabilizers during the polymerization. Coagulation or gel formation is significantly reduced due to the insensitivity of the sterically stabilized system to the fluctuations and increases in electrolyte concentration. In addition, high solids dispersions can be produced by this method due to the higher stabilizing effect of steric stabilizers.

A criteria for polymeric steric stabilizers for ICP dispersion polymerization is that they must be stable during low pH polymerization conditions, stable to oxidizing agents, and that they do not interfere with polymerization of the monomer. An exemplary steric stabilizer is a high molecular weight polyethylene oxide and their copolymers which are preferred as the steric stabilizer due to their stability in low pH reaction conditions. Another exemplary steric stabilizer is polydimethyl siloxane-polyethylene oxide (PDMS-PEO) block copolymer. An advantage of the PDMS-PEO copolymer is that the PDMS block could provide moisture resistance in addition to steric stabilization.

Particularly preferred polymeric steric stabilizers comprise linking groups which, upon formation of a coated layer, crosslink thereby providing an interlinked matrix which functions as a binder thereby providing a coated layer with a suitable structural integrity. Steric stabilizers with a reactive functionality can be employed for post polymerization crosslinking with the polyanion. Any reactive steric stabilizer with a reactive functionality which is stable during the polymerization reaction can be used. Examples of such reactive stabilizers are hydroxyl and dihydroxy end capped polybutadiene. Precursors of reactive steric stabilizer can also be employed for post polymerization activation of the steric stabilizer reactive group.

As used herein, the terminology "steric stabilizer" refers to compounds which are adsorbed to the polymer particles of the dispersion and protective layers around the respective particles to prevent agglomeration of the particles.

Suitable steric stabilizers include, for example, protective colloids and nonionic surfactants having a hydrophilic/lipophilic balance (HLB) greater than about 10. Hydrophilic/lipophilic balance is a measure of the degree to which a material is hydrophilic or lipophilic.

For the purposes of the present invention the Griffin's method is used for determining the hydrophilic/lipophilic balance wherein HLB is defined as:

$$HLB=20*Mh/M$$

wherein:
Mh is the molecular mass of the hydrophilic portion of the molecule and M is the molecular mass of the molecule. An HLB value of greater than about 10 is a water soluble, lipid insoluble, molecule.

Suitable protective colloids include polyethylene oxide, fully hydrolyzed polyvinyl alcohol, partially hydrolyzed poly(vinyl alcohol), poly(vinyl pyrollidone), hydroxyethyl cellulose, polyethylene oxide copolymers and their derivatives, and mixtures thereof. Polyethylene oxide is preferred. Suitable nonionic surfactants include ethoxylated alkyl phenols, ethoxylated acetylenic diols, polyethylene oxide-propylene oxide block copolymers as well as mixtures thereof. Steric stabilizers are preferably added to the polymerization reaction as solutions in water or other polar solvents such as dimethyl sulfoxide, ethylene glycol, N-methyl pyrrolidone, etc.

The stator rotor will be described with reference to FIGS. 5 and 6. A mixer, 20, is illustrated in FIGS. 5 and 5A wherein a paddle mixer, 40, is attached to a shaft, 41, coupled to a motor, 42. As illustrated in FIG. 6, which is a perspective bottom view of the stator rotor, the stator screen, 10, encases the paddle mixer. As the paddle mixer rotates material flows into the interior of the stator screen and is forced out through the holes of the stator screen, as depicted in FIG. 7, thereby causing shear which creates small droplets of monomer. The monomer is then polymerized to form polymer particles with an average particle size which is correlated to the droplet size.

Figure 12:
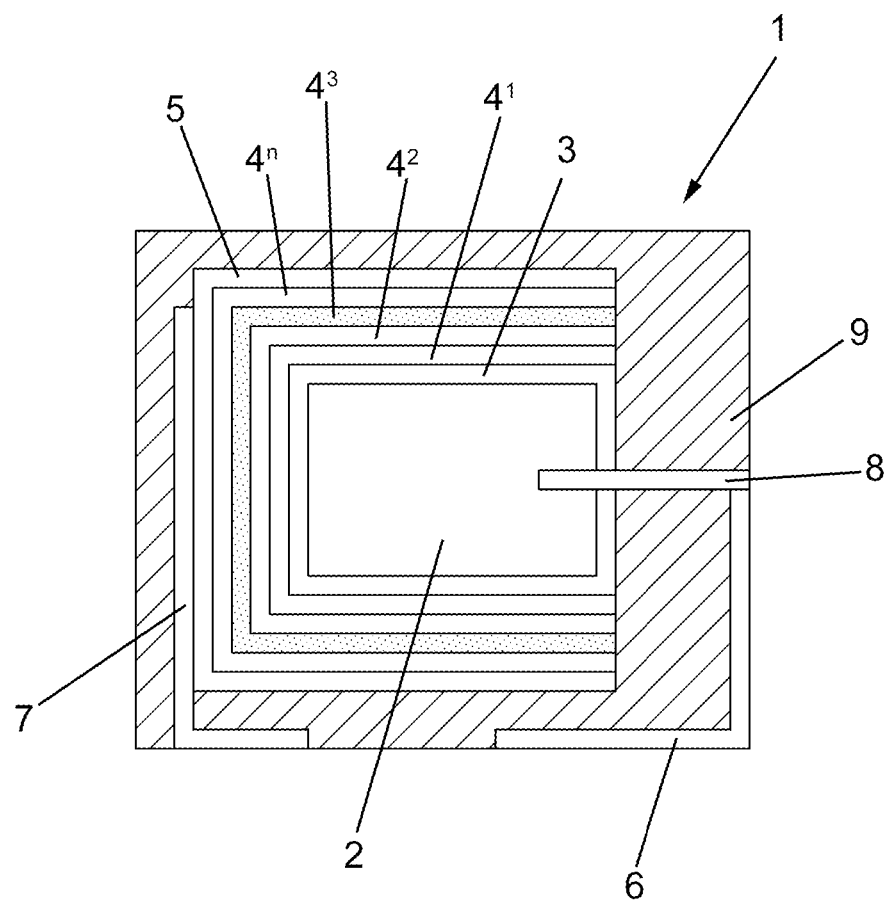
FIG. 12 is a cross-sectional schematic diagram of an embodiment of the invention.

A capacitor of the invention will be described with reference to FIG. 12 wherein a capacitor is illustrated in cross-sectional schematic view. In FIG. 12, the capacitor, 1, comprises an anode, 2, with a dielectric, 3, thereon. After completion the conductive polymeric layer is essentially a continuous preferably un-striated layer, however, it is formed by multiple process steps and will therefore be described herein with each layer discussed separately for the purposes of illustration and clarity.

A first conductive polymer layer, $4^1$, is referred to as an internal layer and is formed in a manner sufficient to allow the interstitial areas of the porous dielectric to be adequately coated. The first conductive layer typically comprises sublayers which are formed sequentially preferably from common components and under common conditions suitable to coat the interstitial areas of the porous dielectric. The first conductive polymer layer typically comprises 1 to 5 layers with each containing a π conjugated conductive polymer comprising monomeric unit from Formula 1 as an essential component thereof. The conducting polymer can be either a water-soluble or water-dispersible compound. Examples of such a π conjugated conductive polymer include polypyrrole or polythiophene. Particularly preferred conductive polymers include poly(3,4-ethylenedioxythiophene), poly(4-(2,3-dihydrothieno-[3,4-b][1,4]dioxin-2-yl)methoxy)-1-butane-sulphonic acid, salt), poly(4-(2,3-dihydrothieno-[3,4-b][1,4]dioxin-2-yl)methoxy)-1-propane-sulphonic acid, salt), poly(4-(2,3-dihydrothieno-[3,4-b][1,4]dioxin-2-yl)methoxy)-1-methyl-1-propane-sulphonic acid, salt), poly(4-(2,3-dihydrothieno-[3,4-b][1,4]dioxin-2-yl)methoxy alcohol, poly(N-methylpyrrole), poly(3-methylpyrrole), poly(3-octylpyrrole), poly(3-decylpyrrole), poly(3-dodecylpyrrole), poly(3,4-dimethylpyrrole), poly(3,4-dibutylpyrrole), poly(3-carboxypyrrole), poly(3-methyl-4-carboxypyrrole), poly(3-methyl-4-carboxyethylpyrrole), poly(3-methyl-4-carboxybutylpyrrole), poly(3-hydroxypyrrole), poly(3-methoxypyrrole), polythiophene, poly(3-methylthiophene), poly(3-hexylthiophene), poly(3-heptylthiophene), poly(3-octylthiophene), poly(3-decylthiophene), poly(3-dodecylthiophene), poly(3-octadecylthiophene), poly(3-bromothiophene), poly(3,4-dimethylthiophene), poly(3,4-dibutylthiophene), poly(3-hydroxythiophene), poly(3-methoxythiophene), poly(3-ethoxythiophene), poly(3-butoxythiophene), poly(3-hexyloxythiophene), poly(3-heptyloxythiophene), poly(3-octyloxythiophene), poly(3-decyloxythiophene), poly(3-dodecyloxythiophene), poly(3-octadecyloxythiophene), poly(3,4-dihydroxythiophene), poly(3,4-dimethoxythiophene), poly(3,4-ethylenedioxythiophene), poly(3,4-propylenedioxythiophene), poly(3,4-butenedioxythiophene), poly(3-carboxythiophene), poly(3-methyl-4-carboxythiophene), poly(3-methyl-4-carboxyethylthiophene), poly(3-methyl-4-carboxybutylthiophene), polyaniline, poly(2-methylaniline), poly(3-isobutylaniline), poly(2-aniline sulfonate), poly(3-aniline sulfonate), and the like.

Among them, (co)polymers composed of one or two kind(s) selected from the group consisting of polypyrrole, polythiophene, poly(4-(2,3-dihydrothieno-[3,4-b][1,4]dioxin-2-yl)methoxy)-1-butane-sulphonic acid, salt), poly(4-(2,3-dihydrothieno-[3,4-b][1,4]dioxin-2-yl)methoxy)-1-methyl-1-propane-sulphonic acid, salt), poly(N-methylpyrrole), poly(3-methylthiophene), poly(3-methoxythiophene), and poly(3,4-ethylenedioxythiophene) etc.

The first conductive polymer layer can be the same as subsequent layers, however, the first conductive polymer layer is preferably formed by at least one application of a conductive polymer formed by in-situ polymerization formed from solutions of monomer(s), oxidant and dopant(s) or by at least one application of a conductive polymer solution or dispersion having small average particle sizes thereby allowing for adequate penetration.

The internal polymer layer may further comprises substances such as surface-active substances, for example ionic and/or nonionic surfactants; adhesion promoters, for example organofunctional silanes or hydrolyzates, phosphates thereof, e.g. 3-glycidoxypropyl-trialkoxysilane, 3-aminopropyltriethoxysilane, 3-mercaptopropyltrimethoxysilane, 3-methacryloyloxy-propyltrimethoxysilane, water soluble monomers/oligomers/polymers containing reactive groups such as acid, alcohol, phenol, amines, epoxy, acrylates etc.

The first conductive layer may further comprises small molecular or polymeric counterions including inventive polyanion.

Subsequent layers of conductive polymer, $4^2$-$4^n$ wherein n is up to about 10, are referred to collectively as external layers typically applied in the form of a dispersion or solution, wherein the conductive polymer containing dispersion or solution used to form each layer may be the same or different thereby resulting in layers which are compositionally the same or different with a preference for commonality for manufacturing convenience. At least one external layer comprises the inventive polyanion as counterion of conductive polymer and preferably each of the external layers comprises the inventive polyanion.

The external layers may also independently comprise further substances such as surface-active substances, for example ionic and/or nonionic surfactants; adhesion promoters, for example organofunctional silanes or hydrolyzates, phosphates thereof, e.g. 3-glycidoxypropyl-trialkoxysilane, 3-aminopropyltriethoxysilane, 3-mercaptopropyltrimethoxysilane, 3-methacryloyloxy-propyltrimethoxysilane, vinyltrimethoxysilane or octyltriethoxysilane, polyurethanes, polyacrylates or polyolefin dispersions, or further additives.

The external layers may further independently comprise additives which enhance the conductivity, for example compounds containing ether groups, for example tetrahydrofuran; compounds containing lactone groups, such as γ-butyrolactone, rvalerolactone; compounds containing amide or lactam groups, such as caprolactam, N-methylcaprolactam, N,N-dimethylacetamide, N-methyl-acetamide, N,N-dimethylformamide (DMF), N-methyl-formamide, N-methylformanilide, N-methylpyrrolidone (NMP), N-octylpyrrolidone, pyrrolidone; sulfones and sulfoxides, for example sulfolane (tetramethylenesulfone), dimethyl sulfoxide (DMSO); sugars or sugar derivatives, for example sucrose, glucose, fructose, lactose, sugar alcohols, for example sorbitol, mannitol; imides, for example succinimide or maleimide; furan derivatives, for example 2-furancarboxylic acid, 3-furancarboxylic acid, and/or di- or polyalcohols, for example ethylene glycol, glycerol or di- or triethylene glycol. Preference is given to using, as conductivity-enhancing additives, ethylene glycol, dimethyl sulfoxide, glycerol or sorbitol.

The conductive polymer solution or dispersion preferably comprises reactive monomers as film formers which can improve polymer film strength upon drying of the film. The reactive monomer or oligomers can be soluble in water or organic solvent or disperse in water through the use of ionic/non-ionic surfactant. The reactive monomers can have average functionalities of at least two or more. The curing process of the monomer can be catalyzed by using heat, radiation or chemical catalysis. Examples of monomers such as compounds having more than one epoxy group includes ethylene glycol diglycidyl ether (EGDGE), propylene glycol diglycidyl ether (PGDGE), 1,4-butanediol diglycidyl ether (BDDGE), pentylene glycol diglycidyl ether, hexylene glycol diglycidyl ether, cyclohexane dimethanol diglycidyl ether, resorcinol glycidyl ether, glycerol diglycidyl ether (GDGE), glycerol polyglycidyl ethers, diglycerol polyglycidyl ethers, trimethylolpropane polyglycidyl ethers, sorbitol diglycidyl ether (Sorbitol-DGE), sorbitol polyglycidyl ethers, polyethylene glycol diglycidyl ether (PEGDGE), polypropylene glycol diglycidyl ether, polytetramethylene glycol diglycidyl ether, di(2,3-epoxypropyl) ether, 1,3-butadiene diepoxide, 1,5-hexadiene diepoxide, 1,2,7,8-diepoxyoctane, 1,2,5,6-diepoxycyclooctane, 4-vinyl cyclohexene diepoxide, bisphenol A diglycidyl ether, maleimide-epoxy compounds, diglycidyl ether, glycidyl acrylate, glycidyl methacrylate, waterborne dispersion of epoxy resins such as bisphenol A epoxy resin, epoxidized Bisphenol A novolac modified epoxy resin, urethane modified Bisphenol A epoxy resin, an epoxidized o-cresylic novolac resin and so forth.

Examples of other film formers are monomers containing acidic groups, i.e. oxalic acid, malonic acid, succinic acid, glutaric acid, adipic acid, pimelic acid, suberic acid, azelaic acid, sebacic acid, dodecanedioic acid, phthalic acids, maleic acid, muconic acid, citric acid, trimesic acid, polyacrylic acid, etc. Particularly preferred organic acids are aromatic acid such as phthalic acid, and particularly orthophthalic acid.

Examples of film forming monomers containing alcohol/acrylate groups, such as, diethylene glycol, pentaerythritol, triethylene glycol, oligo/polyethylene glycol, triethylene glycol monochlorohydrin, diethylene glycol monochlorohydrin, oligo ethylene glycol monochlorohydrin, triethylene glycol monobromohydrin, diethylene glycol monobromohydrin, oligo ethylene glycol monobromohydrin, polyethylene glycol, polyether, polyethylene oxide, triethylene glycol-dimethylether, tetraethylene glycol-dimethylether, diethylene glycol-dimethylether, diethylene glycol-diethylether-diethylene glycol-dibutylether, dipropylene glycol, tripropylene glycol, polypropylene glycol, polypropylene dioxide, polyoxyethylene alkylether, polyoxyethylene glycerin fatty acid ester, polyoxyethylene fatty acid amide, 2-hydroxyethyl methacrylate, 2-hydroxypropyl methacrylate, n-butoxyethyl methacrylate, n-butoxyethylene glycol methacrylate, methoxytriethylene glycol methacrylate, methoxypolyethylene glycol methacrylate, 2-hydroxyethyl acrylate, 2-hydroxypropyl acrylate, n-butoxyethyl acrylate, n-butoxyethylene glycol acrylate, methoxytriethylene glycol acrylate, methoxypolyethylene glycol acrylate, and the like; bifunctional (meth)acrylate compounds, such as, ethylene glycol di(meth)acrylate, diethylene glycol di(meth)acrylate, triethylene glycol di(meth)acrylate, polyethylene glycol di(meth)acrylate, neopentyl glycol di(meth)acrylate, glycerin di(meth)acrylate, and the like; glycidyl ethers, such as, ethylene glycol diglycidyl ether, glycidyl ether, diethylene glycol diglycidyl ether, triethylene glycol diglycidyl ether, polyethylene glycol diglycidyl ether, propylene glycidyl ether, tripropylene glycidyl ether, polypropylene glycidyl ether, glycerin diglycidyl ether, and the like; glycidyl methacrylate, trimethylolpropane triacrylate, ethylene oxide-modified trimethylolpropane triacrylate, ethylene oxide-modified pentaerythritol triacrylate, ethylene oxide-modified pentaerythritol tetraacrylate, and the like.

The external layers may also independently comprise film forming polyanions containing reactive groups such as epoxy, alcohol, silanes, phosphates, amine, alkene, thiol, alkyne, azide carboxylic acid.

The external layers may also independently comprise, as film formers, linear hyperbranched polymers disclosed in patent U.S. Pat. No. 9,378,898. The external layer comprising a linear-hyperbranched polymer where the linear block has at least two reactive end functional groups selected from hydroxyl groups, amino groups, epoxy, acrylate, acid etc. and where the hyper-branched block comprises polyether-epoxy, polyester-epoxy, polyester-silanol, polyester-acid, polyether-alcohol, polyamide-acid, polyether-acrylate, polyether-silanol and polyester-amine pendant groups.

The external layers may further independently comprise work function modifiers disclosed in U.S. Publ. No. 20150348715 A1. Example of work function modifiers such as organotitanates derivatives selected from the group consisting of di-alkoxy acyl titanate, tri-alkoxy acyl titanate, alkoxy triacyl titantate, alkoxy titantate, neoalkoxy titanate, titanium IV 2,2(bis 2-propenolatomethyl)butanolato, tris neodecanoato-O; titanium IV 2,2(bis 2-propenolatomethyl)butanolato, iris(dodecyl)benzenesulfonato-O; titanium IV 2,2(bis 2-propenolatomethyl)butanolato, tris(dioctyl)phosphato-O; titanium IV 2,2(bis 2-propenolatomethyl)tris(dioctyl)pyrophosphatobutanolato-O; titanium IV 2,2(bis 2-propenolatomethyl)butanolato, tris(2-ethylenediamino) ethylato; and titanium IV 2,2(bis 2-propenolatomethyl) butanolato, tris(3-amino)phenylato being representative neoalkoxy titanates and derivatives thereof. Furthermore, work function modifier can be a compounds consisting of cycloaliphatic epoxy resin, ethylene glycol diglycidyl ether, bisphenol A epoxy resin, bisphenol F epoxy resin, bisphenol S epoxy resin, novolac epoxy resin, aliphatic epoxy resin, Glycidylamine epoxy resin, ethylene glycol diglycidyl ether (EGDGE), propylene glycol diglycidyl ether (PGDGE), 1,4-butanediol diglycidyl ether (BDDGE), pentylene glycol diglycidyl ether, hexylene glycol diglycidyl ether, cyclohexane dimethanol diglycidyl ether, resorcinol glycidyl ether, glycerol diglycidyl ether (GDGE), glycerol polyglycidyl ethers, diglycerol polyglycidyl ethers, trimethylolpropane polyglycidyl ethers, sorbitol diglycidyl ether (Sorbitol-DGE), sorbitol polyglycidyl ethers, polyethylene glycol diglycidyl ether (PEGDGE), polypropylene glycol diglycidyl ether, polytetramethylene glycol diglycidyl ether, di(2, 3-epoxypropyl)ether, 1,3-butadiene diepoxide, 1,5-hexadiene diepoxide, 1,2,7,8-diepoxyoctane, 1,2,5,6-diepoxycyclooctane, 4-vinyl cyclohexene diepoxide, bisphenol A diglycidyl ether, maleimide-epoxy compounds, and derivatives thereof.

External layers may further independently comprise nonionic polymer such as a hydroxy-functional nonionic polymer. The term "hydroxy-functional" generally means that the compound contains at least one hydroxyl functional group. The molecular weight of the hydroxy-functional polymer may be from about 100 to 10,000 grams per mole, in some embodiments from about 200 to 2,000, in some embodiments from about 300 to about 1,200, and in some embodiments, from about 400 to about 800.

Any of a variety of hydroxy-functional nonionic polymers may generally be employed. In one embodiment, for example, the hydroxy-functional polymer is a polyalkylene ether. Polyalkylene ethers may include polyalkylene glycols (e.g., polyethylene glycols, polypropylene glycols polytetramethylene glycols, polyepichlorohydrins, etc.), polyoxetanes, polyphenylene ethers, polyether ketones, and so forth. Polyalkylene ethers are typically predominantly linear, nonionic polymers with terminal hydroxy groups. Particularly suitable are polyethylene glycols, polypropylene glycols and polytetramethylene glycols (polytetrahydrofurans). The diol component may be selected, in particular, from saturated or unsaturated, branched or unbranched, aliphatic dihydroxy compounds containing 5 to 36 carbon atoms or aromatic dihydroxy compounds, such as, for example, pentane-1,5-diol, hexane-1,6-diol, neopentyl glycol, bis-(hydroxymethyl)-cyclohexanes, bisphenol A, dimer diols, hydrogenated dimer diols or even mixtures of the diols mentioned.

In addition to those noted above, other hydroxy-functional nonionic polymers may also be employed. Some examples of such polymers include, for instance, ethoxylated alkylphenols; ethoxylated or propoxylated $C_6$-$C_{24}$ fatty alcohols; polyoxyethylene glycol alkyl ethers having the general formula: $CH_3$—$(CH_2)_{10\text{-}16}$—$(O$—$C_2H_4)_{1\text{-}25}$—$OH$ (e.g., octaethylene glycol monododecyl ether and pentaethylene glycol monododecyl ether); polyoxypropylene glycol alkyl ethers having the general formula: $CH_3$—$(CH_2)_{10\text{-}16}$—$(O$—$C_3H_6)_{1\text{-}25}$—$OH$; polyoxyethylene glycol octylphenol ethers having the following general formula: $C_8$—$H_{17}$—$(C_6H_4)$—$(O$—$C_2H_4)_{1\text{-}25}$—$OH$ (e.g., Triton™ X-100); polyoxyethylene glycol alkylphenol ethers having the following general formula: $C_9$—$H_{19}$—$(C_6H_4)$—$(O$—$C_2H_4)_{1\text{-}25}$—$OH$ (e.g., nonoxynol-9); polyoxyethylene glycol esters of $C_8$-$C_{24}$ fatty acids, such as polyoxyethylene glycol sorbitan alkyl esters (e.g., polyoxyethylene (20) sorbitan monolaurate, polyoxyethylene (20) sorbitan monopalmitate, polyoxyethylene (20) sorbitan monostearate, polyoxyethylene (20) sorbitan monooleate, PEG-20 methyl glucose distearate, PEG-20 methyl glucose sesquistearate, PEG-80 castor oil, and PEG-20 castor oil, PEG-3 castor oil, PEG 600 dioleate, and PEG 400 dioleate) and polyoxyethylene glycerol alkyl esters (e.g., polyoxyethylene-23 glycerol laurate and polyoxyethylene-20 glycerol stearate); polyoxyethylene glycol ethers of $C_8$-$C_{24}$ fatty acids (e.g., polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, polyoxyethylene-20 isohexadecyl ether, polyoxyethylene-15 tridecyl ether, and polyoxyethylene-6 tridecyl ether); block copolymers of polyethylene glycol and so forth.

The conductive polymer solution or dispersion may have a pH of 1 to 14, preference being given to a pH of 1 to 10, particularly preferred is a pH of 1 to 8 with the pH being measured at 25° C. To adjust the pH, bases or acids, for example, can be added to the solutions or dispersions. The bases used may be inorganic bases, for example sodium hydroxide, potassium hydroxide, calcium hydroxide or ammonia, or organic bases, for example ethylamine, diethylamine, triethylamine, propylamine, dipropylamine, tripropylamine, isopropylamine, diisopropylamine, butylamine, dibutylamine, tributylamine, isobutylamine, diisobutylamine, triisobutylamine, 1-methylpropylamine, methylethylamine, bis(1-methyl)propylamine, 1,1-dimethylethylamine, pentylamine, dipentylamine, tripentylamine, 2-pentylamine, 3-pentylamine, 2-methyl-butylamine, 3-methylbutylamine, bis(3-methyl-butylamine), tris(3-methylbutylamine), hexylamine, octylamine, 2-ethylhexylamine, decylamine, N-methyl-butylamine, N-ethylbutylamine, N,N-dimethylethylamine, N,N-dimethylpropyl, N-ethyldiisopropylamine, allylamine, diallylamine, ethanolamine, diethanolamine, triethanolamine, methylethanolamine, methyl-diethanolamine, dimethylethanolamine, diethyl-ethanolamine, N-butylethanolamine, N-butyldiethanol-amine, dibutylethanolamine, cyclohexylethanolamine, cyclohexyldiethanolamine, N-ethylethanolamine, N-propylethanolamine, tert-butylethanolamine, tert-butyl-diethanolamine, propanolamine, dipropanolamine, tripropanolamine or benzylamine, bi-, tri-, or tetra-functional amines. The acids used may be inorganic acids, for example sulfuric acid, phosphoric acid or nitric acid, or organic acids, for example carboxylic or sulfonic acids.

It is well known that attaching a lead to a conductive polymer layer is difficult and it is therefore standard in the art to apply an attachment layer, 5, typically comprising layers containing conductive carbon on the conductive polymer layer and silver containing layers on the carbon containing layer. A cathode lead, 7, is attached to the attachment layer by a conductive adhesive. An anode lead, 6, is attached to a lead wire, 8, typically by welding and the entire assembly, except for portions of the cathode lead and anode lead, are encapsulated in a non-conductive material, 9, such as a resin.

Figure 9:
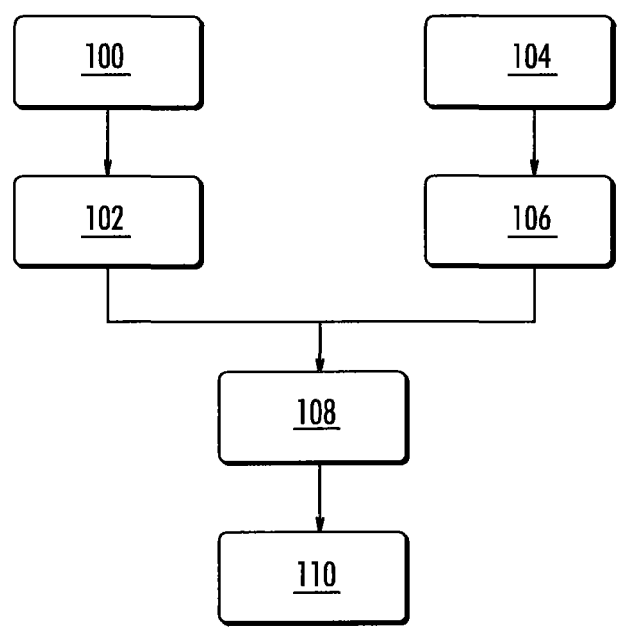
FIG. 9 is a flow chart representation of dispersion preparation.

The process for forming a capacitor will be described with reference to FIG. 9 wherein the process is represented schematically. In FIG. 9, a droplet of monomer is formed at 100 preferably by a stator rotor as defined herein. The droplets are then polymerized preferably in the presence of inventive polyanion formed by the one pot or two step process detailed further herein to form a polymer at 102. An anode is prepared at 104 wherein the anode is a conductor, and preferably a valve metal. A dielectric is formed on the anode at 106 wherein the preferred dielectric is an oxide of the anode. A conductive layer of the polymer is formed on the dielectric at 108 thereby forming a conductive couple with a dielectric there between. The capacitor is finished at 110 wherein finishing can include but is not limited to testing, forming external terminations, encapsulating and the like.

The anode material is not limited herein. A particularly preferred anode material is a metal and a particularly preferred metal is a valve metal or a conductive oxide of a valve metal. Particularly preferred anodes include niobium, aluminum, tantalum and NbO without limit thereto.

The dielectric is not particularly limited herein. A particularly preferred dielectric is an oxide of the anode due to manufacturing considerations.

Throughout the description the term "equivalent hole diameter" or "equivalent diameter" refers to a hole wherein the cross-sectional area is the same as that of a circle with the stated diameter.

Throughout the description terms such as "alkyl", "aryl", "alkylaryl", "arylalkyl" refer to unsubstituted or substituted groups and if already listed as substituted, such as "alkyl alcohol" refer to groups which are not further substituted or may be further substituted.

Test Methods

Determination of % PSSA in Polyanion Copolymer

NMR spectroscopy analysis was used to determine the % PSSA in copolymer; to this end, the peaks at 6.0 to 8.0 ppm correspond to aromatic proton of PSSA and 1.0 to 4.0 ppm (aliphatic proton of copolymer backbone) are considered relative to one another. This gives rise to a ratio of styrene units to acrylate units in the copolymer, which relatively correspond to a % PSSA in polyanion copolymer.

Determination of the Water Absorption Property of Conducting Polymer Dispersion

The conductive polymer film was prepared by dip coating the conductive dispersion on to a glass slide and drying at 150° C. for 30 min. The weight of dry film was recorded. Then, the conductive polymer film was immersed in water for 5 min. The weight of wet film was recorded immediately after gently wiping off residual water on the film. The amount of water absorption was calculated as the difference between wet film and dry film and scaled as shown below:
+=<5% water absorption, ++=5-30% water absorption, +++=>30% water absorption Corners and Edge Coverage Measurement Corner and edge coverage of conducting polymer dispersions on an anodized anode in capacitors was inspected under a microscope and scaled per the following criteria: Edges Not Covered 85%, Corners Not Covered 90%, Half of Corners Covered 95% Corners Appear Completely Covered 99%

Peeling Test in Hot Water

The conductive polymer film was prepared by dip coating the conductive dispersion on a glass slide and drying at 150° C. for 30 min. On the surface of the coating, an incision was made in a reticular pattern using a cutter knife so that the incision reached the glass substrate. The film was then immersed in hot water for 15 min. On the surface of the coating having an incision, a cellophane tape was attached, and then peeled. The peeling situation of the film on glass substrate was visually observed and recorded.

EXAMPLES

In the examples which follow the conductive polymer was poly(3,4-ethylenedioxythiophene) in all cases for consistency.

Synthesis of Polyanion Copolymer

Example 1

Synthesis of poly(4-styrenesulfonic acid-co-hydroxy ethyl acrylate) Sodium Salt

Under an argon atmosphere, a 500 ml flask was initially charged with 33 ml deionized water as a solvent. After adding 8 g styrenesulfonic acid sodium salt, 2 g hydroxyl ethyl acrylate and 1 gm ammonium persulfate, the mixture was saturated with nitrogen by means of a gas inlet tube. To this end, nitrogen was passed through the mixture for 15 min. During this time, the mixture was heated to 70° C. The flask was sealed with a rubber septum and the solution was polymerized for 2 hours. The resulting polyanion copolymer was acidified with dilute sulfuric acid and used directly for preparation of conducting polymer dispersion.

The polyanion copolymer was characterized for % polystyrene sulfonic acid (PSSA) content in polyanion copolymer by $^1$H NMR and summarized in Table 1.

Example 2

Synthesis of poly(4-styrenesulfonic acid-co-acrylamide) Sodium Salt

The polyanion was synthesized using the same procedure as in Example 1 except 8 g styrenesulfonic acid sodium salt, and 2 g acrylamide was used as monomers.

Example 3

The polyanion was synthesized using the same procedure as in Example 2 except the resulting polymer was purified by dialysis in water for 24 hours.

The polyanion copolymer was characterized for % polystyrene sulfonic acid (PSSA) content in polyanion copolymer by $^1$H NMR and summarized in Table 1.

Example 4

Synthesis of poly(4-styrenesulfonic acid-co-Poly(ethylene glycol) methacrylate) Sodium Salt The polyanion was synthesized using the same procedure as mentioned in Example 1 except 5 g styrenesulfonic acid sodium salt, and 5 g poly(ethylene glycol) methacrylate was used as monomers.

Example 5

The polyanion was synthesized using the same procedure as mentioned in Example 2 except the polymer was purified by dialysis in water for 24 hours.

Example 6

The polyanion was synthesized using the same procedure as mentioned in Example 1 except 8 g styrenesulfonic acid sodium salt, and 2 g poly(ethylene glycol) methacrylate was used as monomers.

Example 7

Synthesis of poly(4-styrenesulfonic acid-co-Poly(ethylene glycol) methacrylate-co-glycidyl acrylate) Sodium Salt Dispersion The polyanion dispersion was synthesized using the same procedure as mentioned in Example 1 except 5 g styrenesulfonic acid sodium salt, 5 g poly(ethylene glycol) methacrylate and 10 gm glycidyl acrylate were used as monomers and high shear mixing was used to form dispersion.

The polyanion copolymer was characterized for % polystyrene sulfonic acid (PSSA) content in polyanion copolymer by $^1$H NMR and summarized in Table 1.

TABLE 1

| PSSA CONTENT IN POLYANION COPOLYMER | |
| --- | --- |
| Sample | % PSSA in copolymer |
| Example 1 | 89% |
| Example 3 | 66% |
| Example 5 | 45% |
| Control | 100% |

Preparation of Conducting Polymer Dispersion

Comparison Example 1

2531 g of DI water and 125 g of PSSA 30% (Alfa Aesar) were charged into a 4 L polyethylene bottle. The reaction solution was purged with nitrogen for 0.5-1 hr. The contents were mixed using a rotor-stator mixing system with perforated stator screen with a round hole diameter of 0.6 mm. Subsequently, 28.5 g of 0.1% ferric sulfate solution and 21.5 g of sodium persulfate were then added into the reaction mixture, followed by dropwise addition of 11.25 g of 3,4-ethylenedioxythiophene (EDOT) (Baytron M from Heraeus). The reaction mixture was sheared continuously with a shear speed at 6,000 rpm for 24 hours. 300 g of Lewatit S108H and 300 g of Lewatit MP62WS ion exchange resins were added into the slurry and rolled at around 60 rpm overnight. The conductive polymer dispersion was separated from resins by filtration.

Example 8

A conducting polymer dispersion was prepared in the same manner as in Comparison Example 1 except polyanion from Example 1 was used.

Example 9

A conducting polymer dispersion was prepared in the same manner as Comparison Example 1 except the polyanion from Example 2 was used.

Example 10

A conducting polymer dispersion was prepared in the same manner as Comparison Example 1 except the polyanion from Example 3 was used.

Example 11

A conducting polymer dispersion was prepared in the same manner as Comparison Example 1 except the polyanion from Example 4 was used.

Example 12

A conducting polymer dispersion was prepared in the same manner as Comparison Example 1 except the polyanion from Example 5 was used.

Example 13

Figure 11:
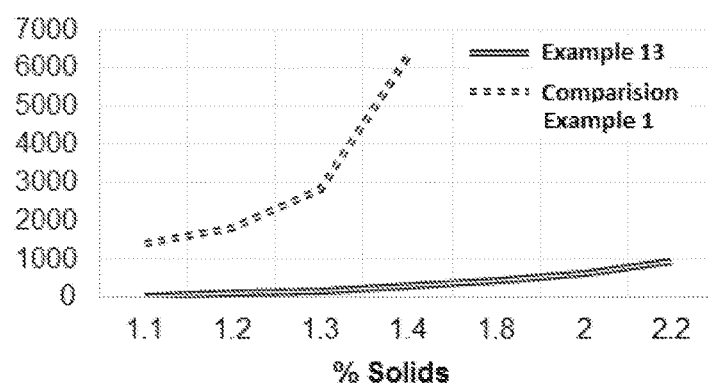
FIG. 11 is a graphical illustration of viscosity as a function of percent solids as in conducting polymer dispersions.

A conducting polymer dispersion was prepared in the same manner as Comparison Example 1 except the polyanion from Example 6 was used and the deionized water (DI water) quantity was adjusted to achieve the desired % solids. The improved polyanion copolymer resulted in high % solids in conducting polymer dispersion at relatively lower viscosity compare to prior-art polyanion as illustrated in FIG. 11.

The water absorption properties of conducting polymer dispersion prepared using polyanion copolymer was measured. As shown in Table 2, the conducting polymer dispersion comprising polyanion copolymer showed varying degrees of water absorption which could be due to differences in their structural composition.

TABLE 2

| WATER ABSORPTION PROPERTIES OF INVENTIVE CONDUCTING POLYMER DISPERSIONS | |
|---|---|
| Sample | Water absorption |
| Example 8 | + |
| Example 10 | +++ |
| Example 12 | + |
| Comparision example 1 | ++ |

Conductive Polymer Dispersion Formulation for Coating on Solid Electrolytic Capacitor

Comparison Example 2

Conducting polymer dispersions from Comparison Example 1 were mixed with DMSO, 3-glycidoxypropylt- rimethoxysilane and reactive monomers containing two epoxy and two carboxylic groups followed by mixing on roller overnight.

Example 14

The coating formulation was prepared in the same manner as Example 2 except the conducting polymer dispersion from Example 8 was used.

Example 15

The coating formulation was prepared in the same manner as Comparison Example 2 except the conducting polymer dispersion from Example 9 was used.

Example 16

The coating formulation was prepared in the same manner as Comparison Example 2 except the conducting polymer dispersion from Example 10 was used.

Example 17

The coating formulation was prepared in the same manner as Comparison Example 2 except the conducting polymer dispersion from Example 11 was used.

Example 18

The coating formulation was prepared in the same manner as comparison Example 2 except the conducting polymer dispersion from Example 12 was used.

Example 19

The coating formulation was prepared in the same manner as comparison Example 2 except the conducting polymer dispersion from Example 13 and waterborne dispersion of reactive monomer/oligomer containing at least three epoxy groups was used.

Example 20

Conducting polymer dispersion from Comparative Example 1 was mixed with DMSO, 3-glycidoxypropylt- rimethoxysilane, polyanion copolymer dispersion from Example 7 followed by mixing on a roller overnight.

Example 21

The coating formulation was prepared in the same manner as Example 19 except polyanion copolymer dispersion from Example 7 was added additionally into the mixture.

Fabrication of Solid Electrolytic Capacitors

Comparison Example 3

A series of tantalum anodes (68 microfarads, 16V) were prepared. The tantalum was anodized to form a dielectric on the tantalum anode. The anodes thus formed was dipped into a solution of iron (III) toluenesulfonate oxidant for 1 minute and sequentially dipped into ethyldioxythiophene monomer for 1 minute to form an anodized anode. The anodized anodes were washed to remove excess monomer and by- products of the reactions after the completion of 60 minutes of polymerization, thereby forming a thin layer of conductive polymer (PEDOT) on the dielectric of the anodized anodes. This process was repeated until a sufficient thickness was achieved.

Conductive polymer dispersion from Comparison Example 2 was applied to form an external polymer layer. After drying, alternating layers of a commercial crosslinker solution, Clevios® K Primer, and conductive polymer dispersion from Comparison Example 2 were applied and repeated 4 times, parts were inspected under microscope for corners and edge coverage. A sequential coating of a graphite layer and a silver layer were applied to produce a solid electrolytic capacitor. Parts were assembled and packaged.

Example 22

A series of tantalum anodes were prepared and tested in a similar fashion as in Comparison Example 3, except that conductive polymer dispersion from Example 14 was applied to form an external polymer layer.

Example 23

A series of tantalum anodes were prepared and tested in a similar fashion as in Comparison Example 3, except that conductive polymer dispersion from Example 15 was applied to form an external polymer layer.

Example 24

A series of tantalum anodes were prepared and tested in a similar fashion as in Comparison Example 3, except that conductive polymer dispersion from Example 16 was applied to form an external polymer layer.

Example 25

A series of tantalum anodes were prepared and tested in a similar fashion as in Comparison Example 3, except that conductive polymer dispersion from Example 17 was applied to form an external polymer layer.

Example 26

A series of tantalum anodes were prepared and tested in a similar fashion as in Comparison Example 3, except that conductive polymer dispersion from Example 18 was applied to form an external polymer layer.

Example 27

A series of tantalum anodes were prepared and tested in a similar fashion as in Comparison Example 3, except that conductive polymer dispersion from Example 19 was applied to form an external polymer layer.

Example 28

A series of tantalum anodes were prepared and tested in a similar fashion as in Comparison Example 26, except that conductive polymer dispersion from Example 19 was applied without use of alternating layers of a commercial crosslinker solution Clevios® K Primer.

Example 29

A series of tantalum anodes were prepared and tested in a similar fashion as in Example 28, except the anode was dipped into a water soluble conductive polymer poly(4-(2,3-dihydrothieno-[3,4-b][1,4]dioxin-2-yl)methoxy)-1-butane-sulphonic acid to form internal layer before applying an external polymer layer.

As described in Table 3, the conducting polymer dispersion comprising inventive polyanion copolymer with adhesion promoter group in Example 27 and 28 showed improvement in polymer coverage in solid electrolytic capacitor. The inventive polyanion also showed excellent ESR stability under 85° C./85% RH load humidity condition.

TABLE 3

ELECTRICAL PERFORMANCE OF INVENTIVE CONDUCTING POLYMER DISPERSION IN SOLID ELECTROLYTIC CAPACITOR

| Sample | % coverage ($3^{rd}$ dip) | ESR (mΩ) | ESR (mΩ) after 85° C./85% RH load humidity test (1000 hrs.) |
|---|---|---|---|
| Example 27 | 99 | 35.0 | 136.8 |
| Example 28 | 99 | 38.2 | 98.4 |
| Comparision Example 3 | 95 | 32.0 | 264.7 |

Table 4 shows the conductivity measurements of polymer dispersion prepared through inventive one pot synthesis process. It was found that significant improvement in conductivity was obtained by the dialysis purification of polyanion copolymer

TABLE 4

EFFECT OF PURIFICATION BY DIALYSIS OF POLYANION COPOLYMER ON CONDUCTIVITY

| Sample | One pot strategy Conductivity (S/cm) | Sample | Two step process Conductivity (S/cm) |
|---|---|---|---|
| Example 15 | 48.9 | Example 16 | 114.7 |
| Example 17 | 7.9 | Example 18 | 66.6 |

As shown in Table 5, It was surprisingly found that some polyanion copolymers dispersion prepared through one pot synthesis strategy demonstrates comparable ESR performance even though it has lower conductivity than dispersion prepared through two step process.

TABLE 5

ELECTRICAL PROPERTIES OF CONDUCTING POLYMER DISPERSIONS PREPARED BY ONE POT(ONE STEP) AND PRIOR ART TWO STEP METHOD

| Sample | One pot strategy ESR (mΩ) | Sample | Two Steps Process ESR (mΩ) |
|---|---|---|---|
| Example 22 | 66.5 | Example 23 | 44.5 |
| Example 25 | 35.6 | Example 26 | 32.0 |

The inventive polyanion copolymer dispersion was also used as a film forming additive in conductive polymer dispersion. The polymer film was tested for electrical conductivity and film strength. As shown in Table 6, surprisingly the polyanion copolymer dispersion as additive in conducting polymer dispersion does not reduce the electrical conductivity and retains good film strength in hot water.

TABLE 6

CONDUCTIVITY AND FILM FORMING PROPERTY OF CONDUCTING POLYMER DISPERSION

| | Conductive polymer dispersion | | | |
|---|---|---|---|---|
| | PEDOT:PSSA | PEDOT:PSSA | PEDOT:PSSA | PEDOT:PSSA |
| Film forming Additive | None | Prior art binder | prior art non polyanion additives | Polyanion copolymer dispersion (Example 7) |
| Conductivity (S/cm) | 200 | 120 | 100 | 180 |
| Peeling after hot water immersion for 15 min? | Yes | Yes | No | No |

The invention has been described with reference to preferred embodiments without limit thereto. One of skill in the art would realize additional embodiments and alterations which are not specifically stated but which are within the scope of the invention as more specifically set forth in the claims appended hereto.

The invention claimed is:

1. A capacitor comprising:
an anode;
a dielectric on said anode; and
a cathode on said dielectric wherein cathode comprises:
a conductive polymer; and
a polyanion wherein said polyanion is a copolymer comprising groups A, B and C represented by the ratio of Formula A:

$$A_xB_yC_z \quad \text{Formula A}$$

wherein:
A is polystyrenesulfonic acid or a salt of polystyrenesulfonate;
B and C separately represent polymerized units substituted by a group selected from:
-Carboxyl group;
—C(O)OR$^6$ group wherein R$^6$ is selected from the group consisting of:
an alkyl of 1 to 20 carbons optionally substituted with a functional group selected from the group consisting of hydroxyl, carboxyl, amine, epoxy, silane, amide, phosphate, imide, thiol, alkene, alkyne, azide, acrylate, anhydride and
—(CHR$^7$CH$_2$O)$_b$—R$^8$ wherein:
R$^7$ is selected from a hydrogen or an alkyl of 1 to 7 carbons;
b is an integer from 1 to the number sufficient to provide a molecular weight of up to 200,000 for the CHR$^7$CH$_2$O— group;
R$^8$ is selected from the group consisting of hydrogen, an alkyl of 1 to 9 carbons optionally substituted with a functional group selected from the group consisting of hydroxyl, carboxyl, amine, epoxy, silane, amide, phosphate, imide, thiol, alkene, alkyne, azide, acrylate and anhydride;
—C(O)—NHR$^9$ group wherein:
R$^9$ is a hydrogen or an alkyl of 1 to 20 carbons optionally substituted with a functional group selected from the group consisting of hydroxyl, carboxyl, amine, epoxy, silane, amide, alcohol, phosphate, imide, thiol, alkene, alkyne, azide, acrylate and anhydride;
—C$_6$H$_4$—R$^{10}$ group wherein:
R$^{10}$ is selected from:
a hydrogen or an alkyl optionally substituted with a functional group selected from the group consisting of hydroxyl, carboxyl, amine, epoxy, silane, amide, phosphate, imide, thiol, alkene, alkyne, azide, acrylate and anhydride;
a reactive group selected from the group consisting of hydroxyl, carboxyl, amine, epoxy, silane, amide, phosphate, imide, thiol, alkene, alkyne, azide, acrylate, anhydride and
—(O(CHR$^{11}$CH$_2$O)$_d$—R$^{12}$ wherein:
R$^{11}$ is a hydrogen or an alkyl of 1 to 7 carbons;
d is an integer from 1 to the number sufficient to provide a molecular weight of up to 200,000 for the CHR$^{11}$CH$_2$O— group;
R$^{12}$ is selected from the group consisting of hydrogen, an alkyl of 1 to 9 carbons optionally substituted with a functional group selected from the group consisting of hydroxyl, carboxyl, amine, epoxy, silane, amide, phosphate, imide, thiol, alkene, alkyne, azide, acrylate and anhydride;
C$_6$H$_4$—O—R$^{13}$ group wherein:
R$^{13}$ is selected from:
a hydrogen, an alkyl optionally substituted with a reactive group selected from the group consisting of hydroxyl, carboxyl, amine, epoxy, silane, amide, alcohol, phosphate and anhydride;
a reactive group selected from the group consisting of epoxy, silane, phosphate alkene, alkyne, azide, acrylate, anhydride and
—(CHR$^{14}$CH$_2$O)$_e$—R$^{15}$ wherein:
R$^{14}$ is a hydrogen or an alkyl of 1 to 7 carbons;
e is an integer from 1 to the number sufficient to provide a molecular weight of up to 200,000 for the —CHR$^{14}$CH$_2$O— group;
R$^{15}$ is selected from the group consisting of a hydrogen and an alkyl of 1 to 9 carbons optionally substituted with a functional group selected from the group consisting of hydroxyl, carboxyl, amine, epoxy, silane, amide, phosphate, imide, thiol, alkene, alkyne, azide, acrylate and anhydride;
x, y and z, taken together are sufficient to form a polyanion with a molecular weight of at least 100 to no more than 500,000 and y/x is 0.01 to 100; z is 0 to a ratio z/x of no more than 100; and
with the proviso that when z is not zero C is not the same group as B and B is not a polymerized monomer of acrylate, methacrylate or an alkoxysilane.

2. The capacitor of claim 1 wherein said polyanion is a random copolymer.

3. The capacitor of claim 1 wherein at least one of $R^7$, $R^{11}$ or $R^{14}$ is selected from hydrogen and methyl.

4. The capacitor of claim 1 wherein x represents 50-99%, y represents 1-50% and z represents 0-49% of the sum total of x+y+z.

5. The capacitor of claim 4 where x represents 70-90%; y represents 10-30% and z represents 0-20% of the sum total of x+y+z.

6. The capacitor of claim 1 wherein x represents 1-40%, y represents 60-99% and z represents 0-39% of the sum total of x+y+z.

7. The capacitor of claim 6 where x represents 5-40%; y represents 60-95% and z represents 0-35% of the sum total of x+y+z.

8. The capacitor of claim 1 wherein said polyanion is selected from the group consisting of:

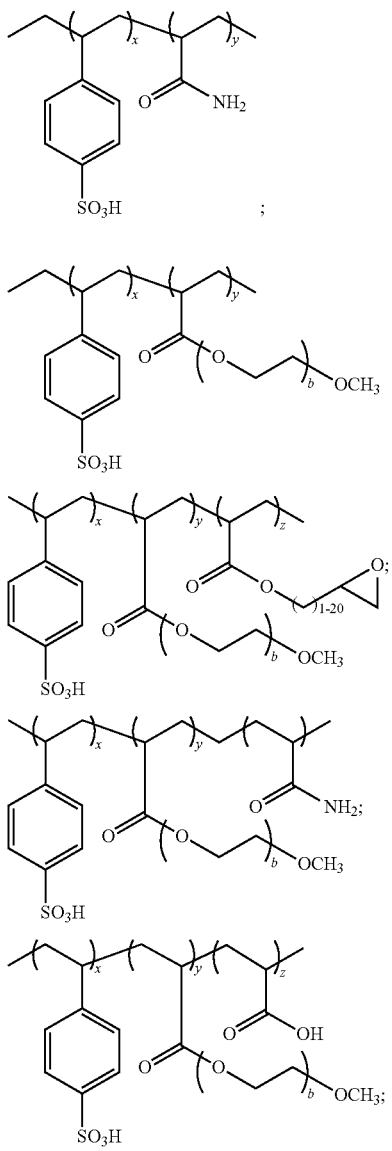

-continued

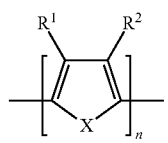

and

9. The capacitor of claim 1 wherein said cathode comprises at least one internal layer and at least one external layer.

10. The capacitor of claim 9 wherein at least one said external layer comprises said polyanion.

11. The capacitor of claim 9 wherein said cathode comprises multiple external layers.

12. The capacitor of claim 11 wherein each said external layer of said external layers comprises said polyanion.

13. The capacitor of claim 1 wherein said conductive polymer is selected from the group consisting of polyaniline, polypyrrole and polythiophene.

14. The capacitor of claim 13 wherein said conductive polymer is conductive polymer comprises repeating units of Formula 1:

Formula 1 wherein:
$R^1$ and $R^2$ independently represent linear or branched $C_1$-$C_{16}$ alkyl or $C_2$-$C_{18}$ alkoxyalkyl; or are $C_3$-$C_8$ cycloalkyl, phenyl or benzyl which are unsubstituted or substituted by $C_1$-$C_6$ alkyl, $C_1$-$C_6$ alkoxy, halogen or $OR^3$; or $R^1$ and $R^2$, taken together, are linear $C_1$-$C_6$ alkylene which is unsubstituted or substituted by $C_1$-$C_6$ alkyl, $C_1$-$C_6$ alkoxy, halogen, $C_3$-$C_8$ cycloalkyl, phenyl, benzyl, $C_1$-$C_4$ alkylphenyl, $C_1$-$C_4$ alkoxyphenyl, halophenyl, $C_1$-$C_4$ alkylbenzyl, $C_1$-$C_4$ alkoxybenzyl or halobenzyl, 5-, 6-, or 7-membered heterocyclic structure containing two oxygen elements, $R^3$ preferably represents hydrogen, linear or branched $C_1$-$C_{16}$ alkyl or $C_2$-$C_{18}$ alkoxyalkyl; or are $C_3$-$C_8$ cycloalkyl, phenyl or benzyl which are unsubstituted or substituted by $C_1$-$C_6$ alkyl; and X is S, N or O.

15. The capacitor of claim 14 wherein X is S.

16. The capacitor of claim 14 wherein $R^1$ and $R^2$ are taken together to represent —O—$(CHR^4)_n$—O— wherein:
n is an integer from 1 to 5;
$R^4$ is independently selected from hydrogen; a linear or branched $C_1$ to $C_{18}$ alkyl radical $C_5$ to $C_{12}$ cycloalkyl radical, $C_6$ to $C_{14}$ aryl radical $C_7$ to $C_{18}$ aralkyl radical or $C_1$ to $C_4$ hydroxyalkyl radical optionally substituted with a functional group selected from carboxylic acid, hydroxyl, amine, substituted amines, alkene, acrylate, thiol, alkyne, azide, sulfate, sulfonate, sufonic acid, imide, amide, epoxy, anhydride, silane, and phosphate; hydroxyl radical; or $R^4$ is selected from —$(CHR^5)_a$—$R^{16}$; —$O(CHR^5)_aR^{16}$; —$CH_2O(CHR^5)_aR^{16}$; —$CH_2O(CH_2CHR^5O)_aR^{16}$; or
$R^4$ is a functional group selected from the group consisting of hydroxyl, carboxyl, amine, epoxy, amide, imide, anhydride, carboxylic acid, hydroxymethyl, alkene, thiol, alkyne, azide, sulfate, sulfonic acid, benzene sulfonic acid, $SO_3M$, anhydride, silane and phosphate;
$R^5$ is H or alkyl chain of 1 to 5 carbons optionally substituted with a functional groups selected from carboxylic acid, hydroxyl, amine, alkene, thiol, alkyne, azide, imide, epoxy, silane, phosphate, acrylate and anhydride;
$R^{16}$ is H or $SO_3M$ or an alkyl chain of 1 to 5 carbons optionally substituted with a functional groups selected from carboxylic acid, hydroxyl, amine, substituted amines, alkene, thiol, alkyne, azide, amide, imide, sulfate, $SO_3M$, amide, epoxy, anhydride, silane, acrylate and phosphate;
a is integer from 0 to 10; and
M is a H or cation preferably selected from ammonia, sodium or potassium.

17. The capacitor of claim 16 wherein n is 2.

18. The capacitor of claim 17 wherein said polymer is 3,4-polyethylene dioxythiophene.

19. The capacitor of claim 1 wherein said anode comprises a valve metal.

20. The capacitor of claim 19 wherein said valve metal is selected from the group consisting of niobium, aluminum, tantalum and NbO.

21. A method for forming a capacitor comprising:
forming an anode;
forming a dielectric on said anode;
forming a cathode on said dielectric wherein said cathode comprises:
a conductive polymer; and
a polyanion wherein said polyanion is a copolymer comprising groups A, B and C represented by the ratio of Formula A:

$$A_xB_yC_z \qquad \text{Formula A}$$

wherein:
A is polystyrenesulfonic acid or a salt of polystyrenesulfonate;
B and C separately represent polymerized units substituted by a group selected from:
-Carboxyl group;
—$C(O)OR^6$ group wherein $R^6$ is selected from the group consisting of:
an alkyl of 1 to 20 carbons optionally substituted with a functional group selected from the group consisting of hydroxyl, carboxyl, amine, epoxy, silane, amide, alcohol, phosphate, imide, thiol, alkene, alkyne, azide, acrylate, anhydride and
—$(CHR^7CH_2O)_b$—$R^8$ wherein:
$R^7$ is selected from a hydrogen or an alkyl of 1 to 7 carbons;
b is an integer from 1 to the number sufficient to provide a molecular weight of up to 200,000 for the —$CHR^7CH_2O$— group;
$R^8$ is selected from the group consisting of hydrogen, an alkyl of 1 to 9 carbons optionally substituted with a functional group selected from the group consisting of hydroxyl, carboxyl, amine, epoxy, silane, amide, phosphate, imide, thiol, alkene, alkyne, azide, acrylate and anhydride;
—$C(O)$—$NHR^9$ group wherein:
$R^9$ is a hydrogen or an alkyl of 1 to 20 carbons optionally substituted with a functional group selected from the group consisting of hydroxyl, carboxyl, amine, epoxy, silane, amide, phosphate, imide, thiol, alkene, alkyne, azide, acrylate and anhydride;
—$C_6H_4$—$R^{10}$ group wherein:
$R^{10}$ is selected from:
a hydrogen or an alkyl optionally substituted with a functional group selected from the group consisting of hydroxyl, carboxyl, amine, epoxy, silane, amide, phosphate, imide, thiol, alkene, alkyne, azide, acrylate and anhydride;
a reactive group selected from the group consisting of hydroxyl, carboxyl, amine, epoxy, silane, amide, alcohol, phosphate, imide, thiols, alkene, alkyne, azide, acrylate, anhydride and —$(O(CHR^{11}CH_2)_d$—$R^{12}$ wherein:
$R^{11}$ is a hydrogen or an alkyl of 1 to 7 carbons;
d is an integer from 1 to the number sufficient to provide a molecular weight of up to 200,000 for the —$CHR^{11}CH_2O$— group;
$R^{12}$ is selected from the group consisting of hydrogen, an alkyl of 1 to 9 carbons optionally substituted with a functional group selected from the group consisting of hydroxyl carboxyl, amine, epoxy, silane, amide, phosphate, imide, thiol, alkene, alkyne, azide, acrylate and anhydride;
—$C_6H_4$—O—$R^{13}$ group wherein:
$R^{13}$ is selected from:
a hydrogen or an alkyl optionally substituted with a reactive group selected from the group consisting of hydroxyl, carboxyl, amine, epoxy, silane, amide, phosphate, imide, thiol, alkene, alkyne, azide, acrylate and anhydride;
a reactive group selected from the group consisting of epoxy, silane, phosphate, alkene, alkyne, acrylate, anhydride and
—$(CHR^{14}CH_2O)_e$—$R^{15}$ wherein:
$R^{14}$ is a hydrogen or an alkyl of 1 to 7 carbons;
e is an integer from 1 to the number sufficient to provide a molecular weight of up to 200,000 for the —$CHR^{14}CH_2O$— group; and R[15] is selected from the group consisting of hydrogen and an alkyl of 1 to 9 carbons optionally substituted with a functional group selected from the group consisting of hydroxyl, carboxyl, amine, epoxy, silane, amide, phosphate, imide, thiol, alkene, alkyne, azide, acrylate and anhydride;

x, y and z, taken together are sufficient to form a polyanion with a molecular weight of at least 100 to no more than 500,000 and y/x is 0.01 to 100; z is 0 to a ratio z/x of no more than 100; and with the proviso that when z is not zero C is not the same group as B and B is not a polymerized monomer of acrylate, methacrylate or an alkoxysilane.

22. The method for forming a capacitor of claim 21 wherein said copolymer is a random copolymer.

23. The method for forming a capacitor of claim 21 wherein at least one of R[7], R[11] or R[14] is selected from hydrogen and methyl.

24. The method for forming a capacitor of claim 21 wherein x represents 50-99%, y represents 1-50% and z represents 0-49% of the sum total of x+y+z.

25. The method for forming a capacitor of claim 24 where x represents 70-90%; y represents 10-30% and z represents 0-20% of the sum total of x+y+z.

26. The method for forming a capacitor of claim 21 wherein x represents 1-40%, y represents 60-99% and z represents 0-39% of the sum total of x+y+z.

27. The method for forming a capacitor of claim 26 where x represents 5-40%; y represents 60-95% and z represents 0-35% of the sum total of x+y+z.

28. The method for forming a capacitor of claim 21 wherein said forming of said cathode further comprises forming said polyanion.

29. The method for forming a capacitor of claim 28 wherein said forming said polyanion comprises polymerization of monomers in the presence of an initiator.

30. The method for forming a capacitor of claim 28 wherein said forming said cathode comprises forming said conductive polymer in the presence of said polyanion.

31. The method for forming a capacitor of claim 30 further comprising purifying said polyanion prior to said forming said conductive polymer.

32. The method for forming a capacitor of the claim 30 wherein said forming of said conductive polymer does not include purifying said polyanion prior to said forming said conductive polymer.

33. The method for forming a capacitor of claim 30 wherein said polyanion is in a mixture further comprising a film forming additive.

34. The method for forming a capacitor of claim 33 wherein film forming additive is selected from the group consisting of monomer, oligomer, linear hyperbranched polymer and polyanion.

35. The method for forming a capacitor of claim 28 wherein said forming said polyanion comprises polymerization of monomers in the presence of an initiator at a shear rate of 10,000-800,000 sec$^{-1}$.

36. The method for forming a capacitor of claim 35 wherein said forming said polyanion comprises polymerization of monomers in the presence of an initiator at a shear rate of 40,000-75,000 sec$^{-1}$.

37. The method for forming a capacitor of claim 21 wherein said polyanion is selected from the group consisting of:

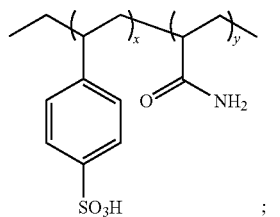

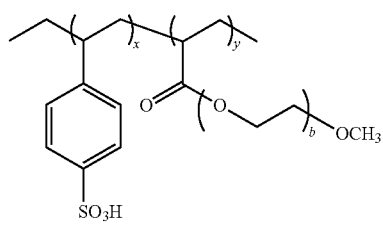

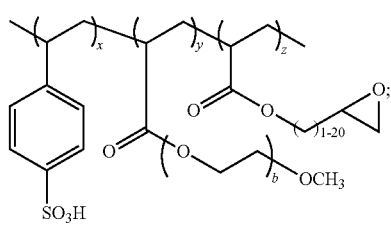

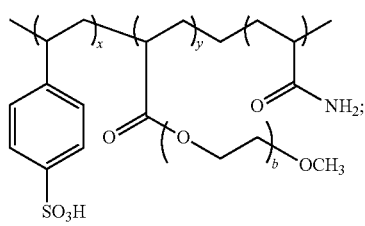

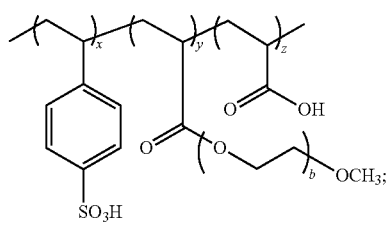

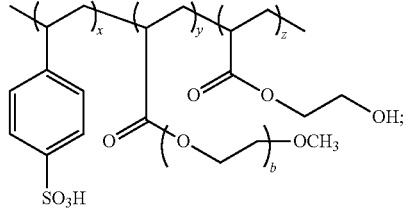

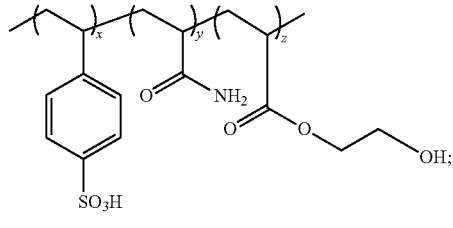

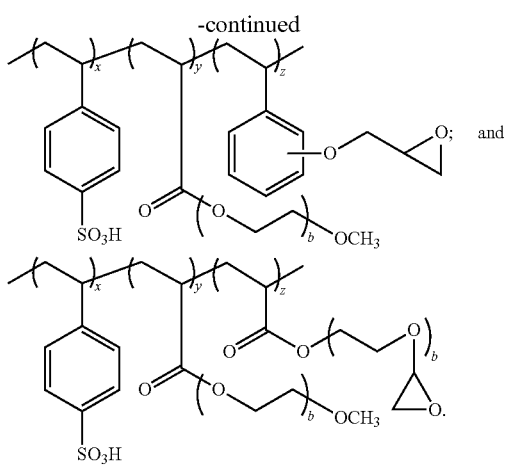

38. The method for forming a capacitor of claim 21 wherein said conductive polymer is selected from the group consisting of polyaniline, polypyrrole and polythiophene.

39. The method for forming a capacitor of claim 38 wherein said conductive polymer comprises repeating units of Formula 1:

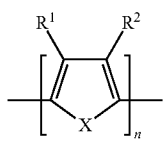

wherein:
$R^1$ and $R^2$ independently represent linear or branched $C_1$-$C_{16}$ alkyl or $C_2$-$C_{18}$ alkoxyalkyl; or are $C_3$-$C_8$ cycloalkyl, phenyl or benzyl which are unsubstituted or substituted by $C_1$-$C_6$ alkyl, $C_1$-$C_6$ alkoxy, halogen or $OR^3$; or $R^1$ and $R^2$, taken together, are linear $C_1$-$C_6$ alkylene which is unsubstituted or substituted by $C_1$-$C_6$ alkyl, $C_1$-$C_6$ alkoxy, halogen, $C_3$-$C_8$ cycloalkyl, phenyl, benzyl, $C_1$-$C_4$ alkylphenyl, $C_1$-$C_4$ alkoxyphenyl, halophenyl, $C_1$-$C_4$alkylbenzyl, $C_1$-$C_4$alkoxybenzyl or halobenzyl, 5-, 6-, or 7-membered heterocyclic structure containing two oxygen elements, $R^3$ preferably represents hydrogen, linear or branched $C_1$-$C_{16}$ alkyl or $C_2$-$C_{18}$ alkoxyalkyl; or are $C_3$-$C_8$ cycloalkyl, phenyl or benzyl which are unsubstituted or substituted by $C_1$-$C_6$ alkyl; and
X is S, N or O.

40. The method for forming a capacitor of claim 39 wherein X is S.

41. The method for forming a capacitor of claim 39 wherein $R^1$ and $R^2$ are taken together to represent —O—$(CHR^4)_n$—O— wherein:
n is an integer from 1 to 5;
$R^4$ is independently selected from hydrogen; a linear or branched $C_1$ to $C_{18}$ alkyl radical $C_5$ to $C_{12}$ cycloalkyl radical, $C_6$ to $C_{14}$ aryl radical $C_7$ to $C_{18}$ aralkyl radical or $C_1$ to $C_4$ hydroxyalkyl radical optionally substituted with a functional group selected from carboxylic acid, hydroxyl, amine, substituted amines, alkene, acrylate, thiol, alkyne, azide, sulfate, sulfonate, sulfonic acid, imide, amide, epoxy, anhydride, silane, and phosphate; hydroxyl radical; or $R^4$ is selected from —$(CHR^5)_a$—$R^{16}$; —$O(CHR^5)_aR^{16}$; —$CH_2O(CHR^5)_aR^{16}$; —$CH_2O(CH_2CHR^5O)_aR^{16}$; or
$R^4$ is a functional group selected from the group consisting of hydroxyl, carboxyl, amine, epoxy, amide, imide, anhydride, hydroxymethyl, carboxylic acid, hydroxymethyl, alkene, thiol, alkyne, azide, sulfate, sulfonic acid, benzene sulfonic acid, $SO_3M$, anhydride, silane, acrylate and phosphate;
$R^5$ is H or alkyl chain of 1 to 5 carbons optionally substituted with a functional groups selected from carboxylic acid, hydroxyl, amine, alkene, thiol, alkyne, azide, imide, epoxy, acrylate, silane, anhydride and phosphate;
$R^{16}$ is H or $SO_3M$ or an alkyl chain of 1 to 5 carbons optionally substituted with a functional groups selected from carboxylic acid, hydroxyl, amine, substituted amines, alkene, thiol, alkyne, azide, amide, imide, sulfate, $SO_3M$, amide, epoxy, anhydride, silane, acrylate and phosphate;
a is from 0 to 10; and
M is a H or cation preferably selected from ammonia, sodium or potassium.

42. The method for forming a capacitor of claim 39 wherein n is 2.

43. The method for forming a capacitor of claim 42 wherein said polymer is 3,4-polyethylene dioxythiophene.

44. The method for forming a capacitor of claim 21 wherein said anode comprises a valve metal.

45. The method for forming a capacitor of claim 44 wherein said valve metal is selected from the group consisting of niobium, aluminum, tantalum and NbO.

46. The method for forming a capacitor of claim 21 wherein said polyanion comprises at least one cross linkable group.

47. The method for forming a capacitor of claim 46 further comprises cross-linking at least one said cross linkable group.

48. The method for forming a capacitor of claim 21 wherein said forming of said cathode comprises forming at least one internal layer and at least one external layer.

49. The method for forming a capacitor of claim 48 wherein said forming of said cathode comprises application of a dispersion comprising said conductive polymer and said polyanion.

50. The method for forming a capacitor of claim 49 wherein said dispersion has a viscosity of at least 200 cP@20 RPM to no more than 4000 cP@20 RPM at ambient temperature.

51. The method for forming a capacitor of claim 50 wherein said dispersion has a viscosity of at least 600 cP@20 RPM to no more than 2000 cP@20 RPM at ambient temperature.

52. The method for forming a capacitor of claim 49 wherein said dispersion has a preferred percent solids of 1 wt % to no more than 5 wt %.

53. The method for forming a capacitor of claim 52 wherein said dispersion has a preferred percent solids of at least 2 wt % to no more than 3.5 wt %.

54. The method for forming a capacitor of claim 49 wherein said dispersion has a percent solids above 1.5 wt % and viscosity of below 2000 cP@20 RPM at ambient temperature.

55. The method for forming a capacitor of claim 48 wherein said forming of said internal layer comprise applying a conductive polymer with a average particle size below 100 nm.

56. The method for forming a capacitor of claim 55 wherein said average particle size is below 50 nm.

57. The method for forming a capacitor of claim 48 wherein at least one said external layer comprises said polyanion.

58. The method for forming a capacitor of claim 48 wherein said cathode comprises multiple external layers.

59. The method for forming a capacitor of claim 58 wherein each said external layer of said external layers comprises said polyanion.

60. The method for forming a capacitor of claim 21 wherein at least one layer of said cathode is formed without primer.

61. A capacitor comprising:
an anode;
a dielectric on said anode; and
a cathode on said dielectric wherein cathode comprises:
a conductive polymer; and
a polyanion wherein said polyanion is a copolymer comprising groups A, B and C represented by the ratio of Formula A:

$$A_xB_yC_z \qquad \text{Formula A}$$

wherein:
A is polystyrenesulfonic acid or a salt of polystyrenesulfonate;
B and C separately represent polymerized units substituted by a group selected from:
-Carboxyl group;
—C(O)OR$^6$ group wherein R$^6$ is selected from the group consisting of:
an alkyl of 1 to 20 carbons substituted with a functional group selected from the group consisting of, carboxyl, amine, amide, phosphate, imide, thiol, alkene, alkyne, azide, acrylate, anhydride and
—(CHR$^7$CH$_2$O)$_b$—R$^8$ wherein:
R$^7$ is a hydrogen;
b is an integer from 1 to the number sufficient to provide a molecular weight of up to 200,000 for the —CHR$^7$CH$_2$O— group;
R$^8$ is a phosphate group;
—C(O)—NHR$^9$ group wherein:
R$^9$ is a hydrogen or an alkyl of 1 to 20 carbons optionally substituted with a functional group selected from the group consisting of hydroxyl, carboxyl, amine, epoxy, silane, amide, alcohol, phosphate, imide, thiol, alkene, alkyne, azide, acrylate and anhydride;
—C$_6$H$_4$—R$^{10}$ group wherein:
R$^{10}$ is selected from:
a hydrogen or an alkyl optionally substituted with a functional group selected from the group consisting of hydroxyl, carboxyl, amine, epoxy, silane, amide, phosphate, imide, thiol, alkene, alkyne, azide, acrylate and anhydride;
a reactive group selected from the group consisting of hydroxyl, carboxyl, amine, epoxy, silane, amide, phosphate, imide, thiol, alkene, alkyne, azide, acrylate, anhydride and
—(O(CHR$^{11}$CH$_2$O)$_d$—R$^{12}$ wherein:
R$^{11}$ is a hydrogen or an alkyl of 1 to 7 carbons;
d is an integer from 1 to the number sufficient to provide a molecular weight of up to 200,000 for the —CHR$^{11}$CH$_2$O— group;
R$^{12}$ is selected from the group consisting of hydrogen, an alkyl of 1 to 9 carbons optionally substituted with a functional group selected from the group consisting of hydroxyl, carboxyl, amine, epoxy, silane, amide, phosphate, imide, thiol, alkene, alkyne, azide, acrylate and anhydride;
—C$_6$H$_4$—O—R$^{13}$ group wherein:
R$^{13}$ is selected from:
a hydrogen, an alkyl optionally substituted with a reactive group selected from the group consisting of hydroxyl, carboxyl, amine, epoxy, silane, amide, alcohol, phosphate and anhydride;
a reactive group selected from the group consisting of epoxy, silane, phosphate alkene, alkyne, azide, acrylate, anhydride and
—(CHR$^{14}$CH$_2$O)$_e$—R$^{15}$ wherein:
R$^{14}$ is a hydrogen or an alkyl of 1 to 7 carbons;
e is an integer from 1 to the number sufficient to provide a molecular weight of up to 200,000 for the —CHR$^{14}$CH$_2$O— group;
R$^{15}$ is selected from the group consisting of a hydrogen and an alkyl of 1 to 9 carbons optionally substituted with a functional group selected from the group consisting of hydroxyl, carboxyl, amine, epoxy, silane, amide, phosphate, imide, thiol, alkene, alkyne, azide, acrylate and anhydride; and
x, y and z, taken together are sufficient to form a polyanion with a molecular weight of at least 100 to no more than 500,000 and y/x is 0.01 to 100; z is 0 to a ratio z/x of no more than 100.

62. The capacitor of claim 61 wherein said polyanion is a random copolymer.

63. The capacitor of claim 61 wherein at least one of R$^7$, R$^{11}$ or R$^{14}$ is selected from hydrogen and methyl.

64. The capacitor of claim 61 wherein x represents 50-99%, y represents 1-50% and z represents 0-49% of the sum total of x+y+z.

65. The capacitor of claim 64 where x represents 70-90%; y represents 10-30% and z represents 0-20% of the sum total of x+y+z.

66. The capacitor of claim 61 wherein x represents 1-40%, y represents 60-99% and z represents 0-39% of the sum total of x+y+z.

67. The capacitor of claim 66 where x represents 5-40%; y represents 60-95% and z represents 0-35% of the sum total of x+y+z.

68. The capacitor of claim 61 wherein said polyanion is selected from the group consisting of:

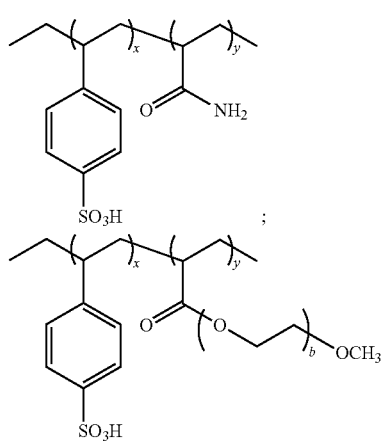

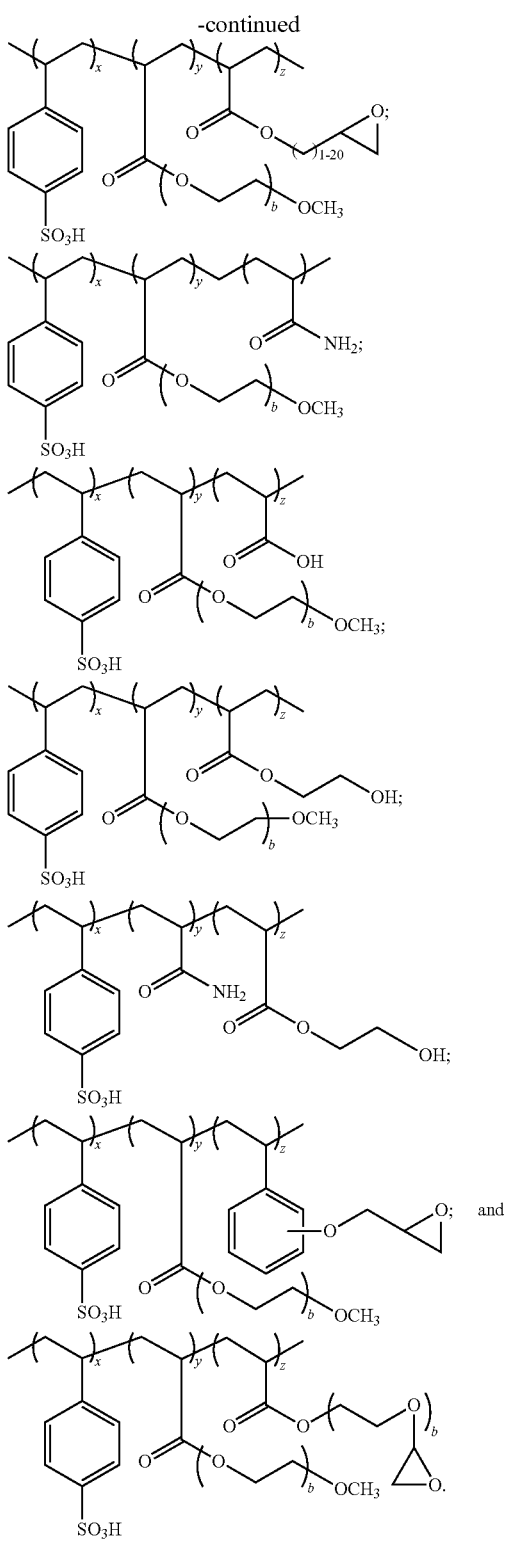

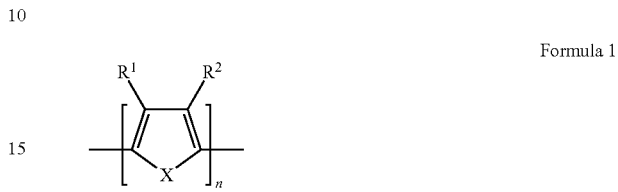

69. The capacitor of claim 61 wherein said cathode comprises at least one internal layer and at least one external layer.

70. The capacitor of claim 69 wherein at least one said external layer comprises said polyanion.

71. The capacitor of claim 69 wherein said cathode comprises multiple external layers.

72. The capacitor of claim 71 wherein each said external layer of said external layers comprises said polyanion.

73. The capacitor of claim 61 wherein said conductive polymer is selected from the group consisting of polyaniline, polypyrrole and polythiophene.

74. The capacitor of claim 73 wherein said conductive polymer is conductive polymer comprises repeating units of Formula 1:

Formula 1 wherein:
$R^1$ and $R^2$ independently represent linear or branched $C_1$-$C_{16}$ alkyl or $C_2$-$C_{18}$ alkoxyalkyl; or are $C_3$-$C_8$ cycloalkyl, phenyl or benzyl which are unsubstituted or substituted by $C_1$-$C_6$ alkyl, $C_1$-$C_6$ alkoxy, halogen or $OR^3$; or $R^1$ and $R^2$, taken together, are linear $C_1$-$C_6$ alkylene which is unsubstituted or substituted by $C_1$-$C_6$ alkyl, $C_1$-$C_6$ alkoxy, halogen, $C_3$-$C_8$ cycloalkyl, phenyl, benzyl, $C_1$-$C_4$ alkylphenyl, $C_1$-$C_4$ alkoxyphenyl, halophenyl, $C_1$-$C_4$alkylbenzyl, $C_1$-$C_4$alkoxybenzyl or halobenzyl, 5-, 6-, or 7-membered heterocyclic structure containing two oxygen elements, $R^3$ preferably represents hydrogen, linear or branched $C_1$-$C_{16}$ alkyl or $C_2$-$C_{18}$ alkoxyalkyl; or are $C_3$-$C_8$ cycloalkyl, phenyl or benzyl which are unsubstituted or substituted by $C_1$-$C_6$ alkyl; and
X is S, N or O.

75. The capacitor of claim 74 wherein X is S.

76. The capacitor of claim 74 wherein $R^1$ and $R^2$ are taken together to represent —O—$(CHR^4)_n$—O— wherein:
n is an integer from 1 to 5;
$R^4$ is independently selected from hydrogen; a linear or branched $C_1$ to $C_{18}$ alkyl radical $C_5$ to $C_{12}$ cycloalkyl radical, $C_6$ to $C_{14}$ aryl radical $C_7$ to $C_{18}$ aralkyl radical or $C_1$ to $C_4$ hydroxyalkyl radical optionally substituted with a functional group selected from carboxylic acid, hydroxyl, amine, substituted amines, alkene, acrylate, thiol, alkyne, azide, sulfate, sulfonate, sufonic acid, imide, amide, epoxy, anhydride, silane, and phosphate; hydroxyl radical; or $R^4$ is selected from —$(CHR^5)_a$—$R^{16}$; $O(CHR^5)_a R^{16}$; —$CH_2O(CHR^5)_a R^{16}$; —$CH_2O(CH_2CHR^5O)_a R^{16}$; or
$R^4$ is a functional group selected from the group consisting of hydroxyl, carboxyl, amine, epoxy, amide, imide, anhydride, carboxylic acid, hydroxymethyl, alkene, thiol, alkyne, azide, sulfate, sulfonic acid, benzene sulfonic acid, $SO_3M$, anhydride, silane and phosphate;
$R^5$ is H or alkyl chain of 1 to 5 carbons optionally substituted with a functional groups selected from carboxylic acid, hydroxyl, amine, alkene, thiol, alkyne, azide, imide, epoxy, silane, phosphate, acrylate and anhydride;
$R^{16}$ is H or $SO_3M$ or an alkyl chain of 1 to 5 carbons optionally substituted with a functional groups selected from carboxylic acid, hydroxyl, amine, substituted amines, alkene, thiol, alkyne, azide, amide, imide, sulfate, $SO_3M$, amide, epoxy, anhydride, silane, acrylate and phosphate;
a is integer from 0 to 10; and M is a H or cation preferably selected from ammonia, sodium or potassium.

77. The capacitor of claim 76 wherein n is 2.

78. The capacitor of claim 77 wherein said polymer is 3,4-polyethylene dioxythiophene.

79. The capacitor of claim 61 wherein said anode comprises a valve metal.

80. The capacitor of claim 79 wherein said valve metal is selected from the group consisting of niobium, aluminum, tantalum and NbO.

81. A method for forming a capacitor comprising:
forming an anode;
forming a dielectric on said anode;
forming a cathode on said dielectric wherein said cathode comprises:
a conductive polymer; and
a polyanion wherein said polyanion is a copolymer comprising groups A, B and C represented by the ratio of Formula A:

$$A_xB_yC_z \quad \text{Formula A}$$

wherein:
A is polystyrenesulfonic acid or a salt of polystyrenesulfonate;
B and C separately represent polymerized units substituted by a group selected from:
-Carboxyl group;
—C(O)OR$^6$ group wherein R$^6$ is selected from the group consisting of:
an alkyl of 1 to 20 carbons substituted with a functional group selected from the group consisting of, carboxyl, amine, amide, phosphate, imide, thiol, alkene, alkyne, azide, acrylate, anhydride and
—(CHR$^7$CH$_2$O)$_b$—R$^8$ wherein:
R$^7$ is selected from a hydrogen or an alkyl of 1 to 7 carbons;
b is an integer from 1 to the number sufficient to provide a molecular weight of up to 200,000 for the —CHR$^7$CH$_2$O— group;
R$^8$ is selected from the group consisting of hydrogen, an alkyl of 1 to 9 carbons optionally substituted with a functional group selected from the group consisting of hydroxyl, carboxyl, amine, epoxy, silane, amide, phosphate, imide, thiol, alkene, alkyne, azide, acrylate and anhydride;
—C(O)—NHR$^9$ group wherein:
R$^9$ is a hydrogen or an alkyl of 1 to 20 carbons optionally substituted with a functional group selected from the group consisting of hydroxyl, carboxyl, amine, epoxy, silane, amide, phosphate, imide, thiol, alkene, alkyne, azide, acrylate and anhydride;
—C$_6$H$_4$—R$^{10}$ group wherein:
R$^{10}$ is selected from:
a hydrogen or an alkyl optionally substituted with a functional group selected from the group consisting of hydroxyl, carboxyl, amine, epoxy, silane, amide, phosphate, imide, thiol, alkene, alkyne, azide, acrylate and anhydride;
a reactive group selected from the group consisting of hydroxyl, carboxyl, amine, epoxy, silane, amide, alcohol, phosphate, imide, thiols, alkene, alkyne, azide, acrylate, anhydride and
—(O(CHR$^{11}$CH$_2$O)$_d$—R$^{12}$ wherein:
R$^{11}$ is a hydrogen or an alkyl of 1 to 7 carbons;
d is an integer from 1 to the number sufficient to provide a molecular weight of up to 200,000 for the —CHR$^{11}$CH$_2$O— group;
R$^{12}$ is selected from the group consisting of hydrogen, an alkyl of 1 to 9 carbons optionally substituted with a functional group selected from the group consisting of hydroxyl carboxyl, amine, epoxy, silane, amide, phosphate, imide, thiol, alkene, alkyne, azide, acrylate and anhydride;
—C$_6$H$_4$—O—R$^{13}$ group wherein:
R$^{13}$ is selected from:
a hydrogen or an alkyl optionally substituted with a reactive group selected from the group consisting of hydroxyl, carboxyl, amine, epoxy, silane, amide, phosphate, imide, thiol, alkene, alkyne, azide, acrylate and anhydride;
a reactive group selected from the group consisting of epoxy, silane, phosphate, alkene, alkyne, acrylate, anhydride and
—(CHR$^{14}$CH$_2$O)$_e$—R$^{15}$ wherein:
R$^{14}$ is a hydrogen or an alkyl of 1 to 7 carbons;
e is an integer from 1 to the number sufficient to provide a molecular weight of up to 200,000 for the —CHR$^{14}$CH$_2$O— group; and
R$^{15}$ is selected from the group consisting of hydrogen and an alkyl of 1 to 9 carbons optionally substituted with a functional group selected from the group consisting of hydroxyl, carboxyl, amine, epoxy, silane, amide, phosphate, imide, thiol, alkene, alkyne, azide, acrylate and anhydride; and
x, y and z, taken together are sufficient to form a polyanion with a molecular weight of at least 100 to no more than 500,000 and y/x is 0.01 to 100; z is 0 to a ratio z/x of no more than 100.

82. The method for forming a capacitor of claim 81 wherein said copolymer is a random copolymer.

83. The method for forming a capacitor of claim 81 wherein at least one of R$^7$, R$^{11}$ or R$^{14}$ is selected from hydrogen and methyl.

84. The method for forming a capacitor of claim 81 wherein x represents 50-99%, y represents 1-50% and z represents 0-49% of the sum total of x+y+z.

85. The method for forming a capacitor of claim 84 where x represents 70-90%; y represents 10-30% and z represents 0-20% of the sum total of x+y+z.

86. The method for forming a capacitor of claim 81 wherein x represents 1-40%, y represents 60-99% and z represents 0-39% of the sum total of x+y+z.

87. The method for forming a capacitor of claim 86 where x represents 5-40%; y represents 60-95% and z represents 0-35% of the sum total of x+y+z.

88. The method for forming a capacitor of claim 81 wherein said forming of said cathode further comprises forming said polyanion.

89. The method for forming a capacitor of claim 88 wherein said forming said polyanion comprises polymerization of monomers in the presence of an initiator.

90. The method for forming a capacitor of claim 88 wherein said forming said cathode comprises forming said conductive polymer in the presence of said polyanion.

91. The method for forming a capacitor of claim 90 further comprising purifying said polyanion prior to said forming said conductive polymer.

92. The method for forming a capacitor of claim 90 wherein said forming of said conductive polymer does not include purifying said polyanion prior to said forming said conductive polymer.

93. The method for forming a capacitor of claim 90 wherein said polyanion is in a mixture further comprising a film forming additive.

94. The method for forming a capacitor of claim 93 wherein film forming additive is selected from the group consisting of monomer, oligomer, linear hyperbranched polymer and polyanion.

95. The method for forming a capacitor of claim 88 wherein said forming said polyanion comprises polymerization of monomers in the presence of an initiator at a shear rate of 10,000-800,000 sec$^{-1}$.

96. The method for forming a capacitor of claim 95 wherein said forming said polyanion comprises polymerization of monomers in the presence of an initiator at a shear rate of 40,000-75,000 sec$^{-1}$.

97. The method for forming a capacitor of claim 81 wherein said polyanion is selected from the group consisting of:

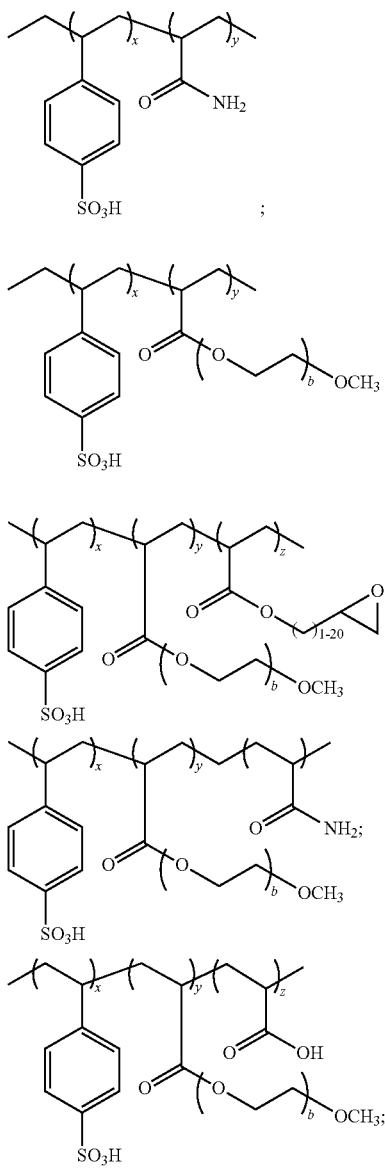

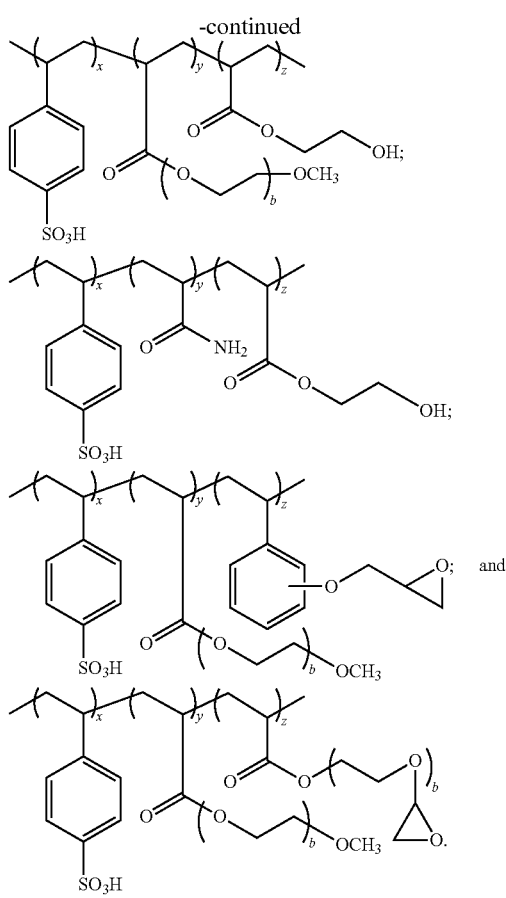

98. The method for forming a capacitor of claim 81 wherein said conductive polymer is selected from the group consisting of polyaniline, polypyrrole and polythiophene.

99. The method for forming a capacitor of claim 98 wherein said conductive polymer comprises repeating units of Formula 1:

Formula 1

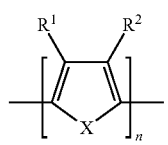

wherein:
R$^1$ and R$^2$ independently represent linear or branched C$_1$-C$_{16}$ alkyl or C$_2$-C$_{18}$ alkoxyalkyl; or are C$_3$-C$_8$ cycloalkyl, phenyl or benzyl which are unsubstituted or substituted by C$_1$-C$_6$ alkyl, C$_1$-C$_6$ alkoxy, halogen or OR$^3$; or R$^1$ and R$^2$, taken together, are linear C$_1$-C$_6$ alkylene which is unsubstituted or substituted by C$_1$-C$_6$ alkyl, C$_1$-C$_6$ alkoxy, halogen, C$_3$-C$_8$ cycloalkyl, phenyl, benzyl, C$_1$-C$_4$ alkylphenyl, C$_1$-C$_4$ alkoxyphenyl, halophenyl, C$_1$-C$_4$alkylbenzyl, C$_1$-C$_4$alkoxybenzyl or halobenzyl, 5-, 6-, or 7-membered heterocyclic structure containing two oxygen elements, R$^3$ preferably represents hydrogen, linear or branched C$_1$-C$_{16}$ alkyl or C$_2$-C$_{18}$ alkoxyalkyl; or are C$_3$-C$_8$ cycloalkyl, phenyl or benzyl which are unsubstituted or substituted by C$_1$-C$_6$ alkyl; and
X is S, N or O.

100. The method for forming a capacitor of claim 99 wherein X is S.

101. The method for forming a capacitor of claim 99 wherein $R^1$ and $R^2$ are taken together to represent —O—$(CHR^4)_n$—O— wherein:

n is an integer from 1 to 5;

$R^4$ is independently selected from hydrogen; a linear or branched $C_1$ to $C_{18}$ alkyl radical $C_5$ to $C_{12}$ cycloalkyl radical, $C_6$ to $C_{14}$ aryl radical $C_7$ to $C_{18}$ aralkyl radical or $C_1$ to $C_4$ hydroxyalkyl radical optionally substituted with a functional group selected from carboxylic acid, hydroxyl, amine, substituted amines, alkene, acrylate, thiol, alkyne, azide, sulfate, sulfonate, sulfonic acid, imide, amide, epoxy, anhydride, silane, and phosphate; hydroxyl radical; or $R^4$ is selected from —$(CHR^5)_a$—$R^{16}$; —$O(CHR^6)_aR^{16}$; —$CH_2O(CHR^5)_aR^{16}$; —$CH_2O(CH_2CHR^5O)_aR^{16}$; or $R^4$ is a functional group selected from the group consisting of hydroxyl, carboxyl, amine, epoxy, amide, imide, anhydride, hdroxymethyl, carboxylic acid, hydroxymethyl, alkene, thiol, alkyne, azide, sulfate, sulfonic acid, benzene sulfonic acid, $SO_3M$, anhydride, silane, acrylate and phosphate;

$R^5$ is H or alkyl chain of 1 to 5 carbons optionally substituted with a functional groups selected from carboxylic acid, hydroxyl, amine, alkene, thiol, alkyne, azide, imide, epoxy, acrylate, silane, anhydride and phosphate;

$R^{16}$ is H or $SO_3M$ or an alkyl chain of 1 to 5 carbons optionally substituted with a functional groups selected from carboxylic acid, hydroxyl, amine, substituted amines, alkene, thiol, alkyne, azide, amide, imide, sulfate, $SO_3M$, amide, epoxy, anhydride, silane, acrylate and phosphate;

a is from 0 to 10; and

M is a H or cation preferably selected from ammonia, sodium or potassium.

102. The method for forming a capacitor of claim 99 wherein n is 2.

103. The method for forming a capacitor of claim 102 wherein said polymer is 3,4-polyethylene dioxythiophene.

104. The method for forming a capacitor of claim 81 wherein said anode comprises a valve metal.

105. The method for forming a capacitor of claim 104 wherein said valve metal is selected from the group consisting of niobium, aluminum, tantalum and NbO.

106. The method for forming a capacitor of claim 81 wherein said polyanion comprises at least one cross linkable group.

107. The method for forming a capacitor of claim 106 further comprises cross-linking at least one said cross linkable group.

108. The method for forming a capacitor of claim 81 wherein said forming of said cathode comprises forming at least one internal layer and at least one external layer.

109. The method for forming a capacitor of claim 108 wherein said forming of said cathode comprises application of a dispersion comprising said conductive polymer and said polyanion.

110. The method for forming a capacitor of claim 109 wherein said dispersion has a viscosity of at least 200 cP@20 RPM to no more than 4000 cP@20 RPM at ambient temperature.

111. The method for forming a capacitor of claim 110 wherein said dispersion has a viscosity of at least 600 cP@20 RPM to no more than 2000 cP@20 RPM at ambient temperature.

112. The method for forming a capacitor of claim 109 wherein said dispersion has a preferred percent solids of 1 wt % to no more than 5 wt %.

113. The method for forming a capacitor of claim 112 wherein said dispersion has a preferred percent solids of of at least 2 wt % to no more than 3.5 wt %.

114. The method for forming a capacitor of claim 109 wherein said dispersion has a percent solids above 1.5 wt % and viscosity of below 2000 cP@20 RPM at ambient temperature.

115. The method for forming a capacitor of claim 108 wherein said forming of said internal layer comprise applying a conductive polymer with a average particle size below 100 nm.

116. The method for forming a capacitor of claim 115 wherein said average particle size is below 50 nm.

117. The method for forming a capacitor of claim 108 wherein at least one said external layer comprises said polyanion.

118. The method for forming a capacitor of claim 108 wherein said cathode comprises multiple external layers.

119. The method for forming a capacitor of claim 118 wherein each said external layer of said external layers comprises said polyanion.

120. The method for forming a capacitor of claim 81 wherein at least one layer of said cathode is formed without primer.

* * * * *